(12) United States Patent
Osborn et al.

(10) Patent No.: US 10,970,936 B2
(45) Date of Patent: Apr. 6, 2021

(54) USE OF NEUROMUSCULAR SIGNALS TO PROVIDE ENHANCED INTERACTIONS WITH PHYSICAL OBJECTS IN AN AUGMENTED REALITY ENVIRONMENT

(71) Applicant: Facebook Technologies, LLC, Menlo Park, CA (US)

(72) Inventors: Christopher Osborn, Brooklyn, NY (US); Mason Remaley, Santa Cruz, CA (US); Lana Awad, Long Island City, NY (US); Adam Berenzweig, Brooklyn, NY (US); Arielle Susu-Mago, Brooklyn, NY (US); Michael Astolfi, Astoria, NY (US); Daniel Wetmore, Brooklyn, NY (US)

(73) Assignee: Facebook Technologies, LLC, Menlo Park, CA (US)

( * ) Notice: Subject to any disclaimer, the term of this patent is extended or adjusted under 35 U.S.C. 154(b) by 0 days.

(21) Appl. No.: 16/593,446

(22) Filed: Oct. 4, 2019

(65) Prior Publication Data

US 2020/0111260 A1    Apr. 9, 2020

Related U.S. Application Data

(60) Provisional application No. 62/741,781, filed on Oct. 5, 2018.

(51) Int. Cl.
*G06T 19/00* (2011.01)
*G06F 3/01* (2006.01)
(Continued)

(52) U.S. Cl.
CPC .......... *G06T 19/006* (2013.01); *A61B 5/1107* (2013.01); *A61B 5/22* (2013.01);
(Continued)

(58) Field of Classification Search
None
See application file for complete search history.

(56) References Cited

U.S. PATENT DOCUMENTS 4,055,168 A    10/1977  Miller et al.
4,896,120 A     1/1990  Kamil
(Continued)

FOREIGN PATENT DOCUMENTS

CA    2902045 A1    8/2014
CA    2921954 A1    2/2015
(Continued)

OTHER PUBLICATIONS

Extended European Search Report for European Application No. EP 17835111.0 dated Nov. 21, 2019.
(Continued)

*Primary Examiner* — David H Chu
(74) *Attorney, Agent, or Firm* — FisherBroyles, LLP

(57) ABSTRACT

Computerized systems, methods, kits, and computer-readable media storing code for implementing the methods are provided for interacting with a physical object in an augmented reality (AR) environment generated by an AR system. One such system includes: a plurality of neuromuscular sensors able to sense a plurality of neuromuscular signals from a user, and at least one computer processor. The neuromuscular sensors are arranged on one or more wearable devices worn by the user to sense the neuromuscular signals. The at least one computer processor is or are programmed to: determine, based at least in part, on the neuromuscular signals sensed by the neuromuscular sensors, information about an interaction of the user with the physical object in the AR environment generated by the AR system; and instruct the AR system to provide feedback
(Continued)

based, at least in part, on the information about the interaction of the user with the physical object.

30 Claims, 11 Drawing Sheets

(51) Int. Cl.
    *A61B 5/22*           (2006.01)
    *A61B 5/11*           (2006.01)
    *G16H 80/00*         (2018.01)
    *G16H 20/30*         (2018.01)
    *A61B 5/00*           (2006.01)

(52) U.S. Cl.
    CPC ............ *A61B 5/4519* (2013.01); *G06F 3/015* (2013.01); *G16H 20/30* (2018.01); *G16H 80/00* (2018.01)

(56) References Cited

U.S. PATENT DOCUMENTS

| | | |
|---|---|---|
| 5,625,577 A | 4/1997 | Kunii et al. |
| 6,005,548 A | 12/1999 | Latypov et al. |
| 6,009,210 A | 12/1999 | Kang |
| 6,244,873 B1 | 6/2001 | Hill et al. |
| 6,411,843 B1 | 6/2002 | Zarychta |
| 6,658,287 B1 | 12/2003 | Litt et al. |
| 6,720,984 B1 | 4/2004 | Jorgensen et al. |
| 6,774,885 B1 | 8/2004 | Even-Zohar |
| 6,942,621 B2 | 9/2005 | Avinash et al. |
| 7,089,148 B1 | 8/2006 | Bachmann et al. |
| 7,351,975 B2 | 4/2008 | Brady et al. |
| 7,574,253 B2 | 8/2009 | Edney et al. |
| 7,580,742 B2 | 8/2009 | Tan et al. |
| 7,787,946 B2 | 8/2010 | Stahmann et al. |
| 7,805,386 B2 | 9/2010 | Greer |
| 7,901,368 B2 | 3/2011 | Flaherty et al. |
| 8,170,656 B2 | 5/2012 | Tan et al. |
| 8,190,249 B1 | 5/2012 | Gharieb et al. |
| 8,311,623 B2 | 11/2012 | Sanger |
| 8,348,538 B2 * | 1/2013 | Van Loenen .......... B43K 5/025 345/179 |
| 8,351,651 B2 | 1/2013 | Lee |
| 8,421,634 B2 | 4/2013 | Tan et al. |
| 8,435,191 B2 | 5/2013 | Barboutis et al. |
| 8,437,844 B2 | 5/2013 | Syed Momen et al. |
| 8,447,704 B2 | 5/2013 | Tan et al. |
| 8,484,022 B1 | 7/2013 | Vanhoucke |
| 8,718,980 B2 | 5/2014 | Garudadri et al. |
| 8,744,543 B2 | 6/2014 | Li et al. |
| 8,754,862 B2 | 6/2014 | Zaliva |
| D717,685 S | 11/2014 | Bailey et al. |
| 8,880,163 B2 | 11/2014 | Barachant et al. |
| 8,890,875 B2 | 11/2014 | Jammes et al. |
| 8,892,479 B2 | 11/2014 | Tan et al. |
| 8,914,472 B1 * | 12/2014 | Lee ................... H04L 29/06476 709/219 |
| 9,037,530 B2 | 5/2015 | Tan et al. |
| D742,272 S | 11/2015 | Bailey et al. |
| 9,218,574 B2 | 12/2015 | Phillipps et al. |
| 9,235,934 B2 | 1/2016 | Mandella et al. |
| 9,240,069 B1 | 1/2016 | Li |
| 9,278,453 B2 | 3/2016 | Assad |
| 9,299,248 B2 | 3/2016 | Lake et al. |
| D756,359 S | 5/2016 | Bailey et al. |
| 9,351,653 B1 | 5/2016 | Harrison |
| 9,367,139 B2 | 6/2016 | Ataee et al. |
| 9,372,535 B2 | 6/2016 | Bailey et al. |
| 9,389,694 B2 | 7/2016 | Ataee et al. |
| 9,408,316 B2 | 8/2016 | Bailey et al. |
| 9,459,697 B2 | 10/2016 | Bedikian et al. |
| 9,483,123 B2 | 11/2016 | Aleem et al. |
| 9,597,015 B2 | 3/2017 | McNames et al. |
| 9,600,030 B2 | 3/2017 | Bailey et al. |
| 9,612,661 B2 | 4/2017 | Wagner et al. |
| 9,613,262 B2 | 4/2017 | Holz |
| 9,654,477 B1 | 5/2017 | Kotamraju |
| 9,659,403 B1 | 5/2017 | Horowitz |
| 9,687,168 B2 | 6/2017 | John |
| 9,696,795 B2 | 7/2017 | Marcolina et al. |
| 9,720,515 B2 | 8/2017 | Wagner et al. |
| 9,741,169 B1 | 8/2017 | Holz |
| 9,766,709 B2 | 9/2017 | Holz |
| 9,785,247 B1 | 10/2017 | Horowitz et al. |
| 9,788,789 B2 | 10/2017 | Bailey |
| 9,864,431 B2 | 1/2018 | Keskin et al. |
| 9,867,548 B2 | 1/2018 | Le et al. |
| 9,880,632 B2 | 1/2018 | Ataee et al. |
| 9,891,718 B2 | 2/2018 | Connor |
| 9,921,641 B1 * | 3/2018 | Worley, III ............. G06F 3/017 |
| 10,042,422 B2 | 8/2018 | Morun et al. |
| 10,070,799 B2 | 9/2018 | Ang et al. |
| 10,078,435 B2 | 9/2018 | Noel |
| 10,101,809 B2 | 10/2018 | Morun et al. |
| 10,152,082 B2 | 12/2018 | Bailey |
| 10,188,309 B2 | 1/2019 | Morun et al. |
| 10,199,008 B2 | 2/2019 | Aleem et al. |
| 10,203,751 B2 | 2/2019 | Keskin et al. |
| 10,216,274 B2 | 2/2019 | Chapeskie et al. |
| 10,251,577 B2 | 4/2019 | Morun et al. |
| 10,310,601 B2 | 6/2019 | Morun et al. |
| 10,331,210 B2 | 6/2019 | Morun et al. |
| 10,362,958 B2 | 7/2019 | Morun et al. |
| 10,409,371 B2 | 9/2019 | Kaifosh et al. |
| 10,437,335 B2 | 10/2019 | Daniels |
| 10,460,455 B2 | 10/2019 | Giurgica-Tiron et al. |
| 10,489,986 B2 | 11/2019 | Kaifosh et al. |
| 10,496,168 B2 | 12/2019 | Kaifosh et al. |
| 10,504,286 B2 | 12/2019 | Kaifosh et al. |
| 2003/0144829 A1 | 7/2003 | Geatz et al. |
| 2003/0171921 A1 | 9/2003 | Manabe et al. |
| 2003/0184544 A1 | 10/2003 | Prudent |
| 2004/0054273 A1 | 3/2004 | Finneran et al. |
| 2004/0092839 A1 | 5/2004 | Shin et al. |
| 2006/0129057 A1 | 6/2006 | Maekawa et al. |
| 2007/0009151 A1 | 1/2007 | Pittman et al. |
| 2007/0172797 A1 | 7/2007 | Hada et al. |
| 2007/0177770 A1 | 8/2007 | Derchak et al. |
| 2007/0256494 A1 | 11/2007 | Nakamura et al. |
| 2007/0285399 A1 | 12/2007 | Lund |
| 2008/0051673 A1 | 2/2008 | Kong et al. |
| 2008/0052643 A1 | 2/2008 | Ike et al. |
| 2008/0103639 A1 | 5/2008 | Troy et al. |
| 2008/0214360 A1 | 9/2008 | Stirling et al. |
| 2008/0221487 A1 | 9/2008 | Zohar et al. |
| 2009/0027337 A1 | 1/2009 | Hildreth |
| 2009/0079813 A1 | 3/2009 | Hildreth |
| 2009/0082692 A1 | 3/2009 | Hale et al. |
| 2009/0082701 A1 | 3/2009 | Zohar et al. |
| 2009/0112080 A1 | 4/2009 | Matthews |
| 2009/0124881 A1 | 5/2009 | Rytky |
| 2009/0326406 A1 | 12/2009 | Tan et al. |
| 2009/0327171 A1 | 12/2009 | Tan et al. |
| 2010/0030532 A1 | 2/2010 | Arora et al. |
| 2010/0063794 A1 | 3/2010 | Hernandez-Rebollar |
| 2010/0106044 A1 | 4/2010 | Linderman |
| 2010/0113910 A1 | 5/2010 | Brauers et al. |
| 2010/0280628 A1 | 11/2010 | Sankai |
| 2010/0292595 A1 | 11/2010 | Paul |
| 2010/0292606 A1 | 11/2010 | Prakash et al. |
| 2010/0292617 A1 | 11/2010 | Lei et al. |
| 2010/0293115 A1 | 11/2010 | Seyed Momen |
| 2010/0315266 A1 | 12/2010 | Gunawardana et al. |
| 2011/0007035 A1 * | 1/2011 | Shai ...................... G06F 3/0312 345/179 |
| 2011/0077484 A1 | 3/2011 | Van Slyke et al. |
| 2011/0092826 A1 | 4/2011 | Lee et al. |
| 2011/0173204 A1 | 7/2011 | Murillo et al. |
| 2011/0205242 A1 * | 8/2011 | Friesen .................. G06F 3/011 345/633 |
| 2011/0230782 A1 | 9/2011 | Bartol et al. |
| 2012/0066163 A1 | 3/2012 | Balls et al. |
| 2012/0188158 A1 | 7/2012 | Tan et al. |

(56) References Cited

U.S. PATENT DOCUMENTS

| | | |
|---|---|---|
| 2012/0265480 A1 | 10/2012 | Oshima |
| 2012/0283526 A1 | 11/2012 | Gommesen et al. |
| 2013/0004033 A1 | 1/2013 | Trugenberger |
| 2013/0038707 A1* | 2/2013 | Cunningham ......... H04N 7/183 348/65 |
| 2013/0077820 A1 | 3/2013 | Marais et al. |
| 2013/0123656 A1 | 5/2013 | Heck |
| 2013/0141375 A1 | 6/2013 | Ludwig et al. |
| 2013/0207889 A1 | 8/2013 | Chang et al. |
| 2013/0217998 A1 | 8/2013 | Mahfouz et al. |
| 2013/0232095 A1 | 9/2013 | Tan et al. |
| 2013/0293580 A1* | 11/2013 | Spivack ............ G06Q 30/0643 345/633 |
| 2013/0317382 A1 | 11/2013 | Le |
| 2013/0317648 A1 | 11/2013 | Assad |
| 2014/0052150 A1 | 2/2014 | Taylor et al. |
| 2014/0092009 A1 | 4/2014 | Yen et al. |
| 2014/0098018 A1 | 4/2014 | Kim et al. |
| 2014/0196131 A1 | 7/2014 | Lee |
| 2014/0198034 A1 | 7/2014 | Bailey et al. |
| 2014/0198035 A1 | 7/2014 | Bailey et al. |
| 2014/0223462 A1 | 8/2014 | Aimone et al. |
| 2014/0240103 A1 | 8/2014 | Lake et al. |
| 2014/0240223 A1 | 8/2014 | Lake et al. |
| 2014/0245200 A1 | 8/2014 | Holz |
| 2014/0249397 A1 | 9/2014 | Lake et al. |
| 2014/0277622 A1 | 9/2014 | Raniere |
| 2014/0278441 A1 | 9/2014 | Ton et al. |
| 2014/0297528 A1 | 10/2014 | Agrawal et al. |
| 2014/0304665 A1 | 10/2014 | Holz |
| 2014/0310595 A1* | 10/2014 | Acharya ............... G06F 9/453 715/706 |
| 2014/0330404 A1 | 11/2014 | Abdelghani et al. |
| 2014/0334083 A1 | 11/2014 | Bailey |
| 2014/0344731 A1 | 11/2014 | Holz |
| 2014/0355825 A1 | 12/2014 | Kim et al. |
| 2014/0358024 A1 | 12/2014 | Nelson et al. |
| 2014/0359540 A1* | 12/2014 | Kelsey .................. G06F 3/017 715/863 |
| 2014/0361988 A1 | 12/2014 | Katz et al. |
| 2014/0364703 A1 | 12/2014 | Kim et al. |
| 2014/0365163 A1 | 12/2014 | Jallon |
| 2014/0376773 A1 | 12/2014 | Holz |
| 2015/0006120 A1 | 1/2015 | Sett et al. |
| 2015/0010203 A1 | 1/2015 | Muninder et al. |
| 2015/0025355 A1 | 1/2015 | Bailey et al. |
| 2015/0029092 A1 | 1/2015 | Holz et al. |
| 2015/0035827 A1 | 2/2015 | Yamaoka et al. |
| 2015/0045689 A1 | 2/2015 | Barone |
| 2015/0045699 A1 | 2/2015 | Mokaya et al. |
| 2015/0051470 A1 | 2/2015 | Bailey et al. |
| 2015/0057770 A1 | 2/2015 | Bailey et al. |
| 2015/0070270 A1 | 3/2015 | Bailey et al. |
| 2015/0070274 A1 | 3/2015 | Morozov |
| 2015/0084860 A1 | 3/2015 | Aleem et al. |
| 2015/0109202 A1 | 4/2015 | Ataee et al. |
| 2015/0124566 A1 | 5/2015 | Lake et al. |
| 2015/0128094 A1 | 5/2015 | Baldwin et al. |
| 2015/0141784 A1 | 5/2015 | Morun et al. |
| 2015/0148641 A1 | 5/2015 | Morun et al. |
| 2015/0157944 A1 | 6/2015 | Gottlieb |
| 2015/0169074 A1 | 6/2015 | Ataee et al. |
| 2015/0182165 A1 | 7/2015 | Miller et al. |
| 2015/0193949 A1 | 7/2015 | Katz et al. |
| 2015/0223716 A1 | 8/2015 | Korkala et al. |
| 2015/0234426 A1 | 8/2015 | Bailey et al. |
| 2015/0242575 A1* | 8/2015 | Abovitz ............... G06F 3/0304 705/2 |
| 2015/0261306 A1 | 9/2015 | Lake |
| 2015/0261318 A1 | 9/2015 | Scavezze et al. |
| 2015/0277575 A1 | 10/2015 | Ataee et al. |
| 2015/0296553 A1 | 10/2015 | DiFranco et al. |
| 2015/0302168 A1 | 10/2015 | De Sapio et al. |
| 2015/0309563 A1 | 10/2015 | Connor |
| 2015/0309582 A1 | 10/2015 | Gupta |
| 2015/0313496 A1 | 11/2015 | Connor |
| 2015/0325202 A1 | 11/2015 | Lake et al. |
| 2015/0332013 A1 | 11/2015 | Lee et al. |
| 2015/0346701 A1 | 12/2015 | Gordon et al. |
| 2015/0366504 A1 | 12/2015 | Connor |
| 2015/0370326 A1 | 12/2015 | Chapeskie et al. |
| 2015/0370333 A1 | 12/2015 | Ataee et al. |
| 2015/0379770 A1* | 12/2015 | Haley, Jr. ............ G02B 27/0172 345/633 |
| 2016/0011668 A1 | 1/2016 | Gilad-Bachrach et al. |
| 2016/0049073 A1 | 2/2016 | Lee |
| 2016/0050037 A1 | 2/2016 | Webb |
| 2016/0071319 A1* | 3/2016 | Fallon ................... G06T 19/006 345/633 |
| 2016/0092504 A1 | 3/2016 | Mitri et al. |
| 2016/0144172 A1 | 5/2016 | Hsueh et al. |
| 2016/0162604 A1 | 6/2016 | Xiaoli et al. |
| 2016/0187992 A1 | 6/2016 | Yamamoto et al. |
| 2016/0217614 A1 | 7/2016 | Kraver et al. |
| 2016/0235323 A1 | 8/2016 | Tadi et al. |
| 2016/0239080 A1 | 8/2016 | Marcolina et al. |
| 2016/0262687 A1 | 9/2016 | Imperial |
| 2016/0274758 A1 | 9/2016 | Bailey |
| 2016/0275726 A1 | 9/2016 | Mullins |
| 2016/0292497 A1 | 10/2016 | Kehtarnavaz et al. |
| 2016/0313798 A1 | 10/2016 | Connor |
| 2016/0313801 A1 | 10/2016 | Wagner et al. |
| 2016/0313890 A1 | 10/2016 | Walline et al. |
| 2016/0313899 A1 | 10/2016 | Noel |
| 2016/0314623 A1* | 10/2016 | Coleman ............... G02B 27/017 |
| 2016/0342227 A1* | 11/2016 | Natzke ................ G06F 3/03545 |
| 2016/0350973 A1* | 12/2016 | Shapira ................ G06T 19/006 |
| 2017/0031502 A1 | 2/2017 | Rosenberg et al. |
| 2017/0035313 A1 | 2/2017 | Hong et al. |
| 2017/0061817 A1 | 3/2017 | Mettler May |
| 2017/0068445 A1 | 3/2017 | Lee et al. |
| 2017/0080346 A1 | 3/2017 | Abbas |
| 2017/0090604 A1 | 3/2017 | Barbier |
| 2017/0091567 A1* | 3/2017 | Wang .................. A61B 5/02028 |
| 2017/0119472 A1 | 5/2017 | Herrmann et al. |
| 2017/0123487 A1 | 5/2017 | Hazra et al. |
| 2017/0124816 A1 | 5/2017 | Yang et al. |
| 2017/0161635 A1 | 6/2017 | Oono et al. |
| 2017/0188980 A1 | 7/2017 | Ash |
| 2017/0237789 A1* | 8/2017 | Harner .................. G06F 3/017 709/205 |
| 2017/0259167 A1 | 9/2017 | Cook et al. |
| 2017/0277282 A1 | 9/2017 | Go |
| 2017/0285756 A1 | 10/2017 | Wang et al. |
| 2017/0285848 A1 | 10/2017 | Rosenberg et al. |
| 2017/0296363 A1 | 10/2017 | Yetkin et al. |
| 2017/0301630 A1 | 10/2017 | Nguyen et al. |
| 2017/0308118 A1 | 10/2017 | Ito |
| 2017/0344706 A1 | 11/2017 | Torres et al. |
| 2017/0347908 A1 | 12/2017 | Watanabe et al. |
| 2018/0000367 A1 | 1/2018 | Longinotti-Buitoni |
| 2018/0018825 A1* | 1/2018 | Kim .................... G06F 3/04842 |
| 2018/0020285 A1* | 1/2018 | Zass .................... G10L 21/028 |
| 2018/0020951 A1 | 1/2018 | Kaifosh et al. |
| 2018/0020978 A1 | 1/2018 | Kaifosh et al. |
| 2018/0024634 A1 | 1/2018 | Kaifosh et al. |
| 2018/0024635 A1 | 1/2018 | Kaifosh et al. |
| 2018/0064363 A1 | 3/2018 | Morun et al. |
| 2018/0067553 A1 | 3/2018 | Morun et al. |
| 2018/0068489 A1* | 3/2018 | Kim ..................... G06Q 50/10 |
| 2018/0074332 A1* | 3/2018 | Li ........................ G06F 1/163 |
| 2018/0081439 A1 | 3/2018 | Daniels |
| 2018/0088765 A1 | 3/2018 | Bailey |
| 2018/0092599 A1 | 4/2018 | Kerth et al. |
| 2018/0093181 A1 | 4/2018 | Goslin et al. |
| 2018/0095542 A1* | 4/2018 | Mallinson ............. G06F 1/163 |
| 2018/0095630 A1 | 4/2018 | Bailey |
| 2018/0101235 A1 | 4/2018 | Bodensteiner et al. |
| 2018/0101289 A1 | 4/2018 | Bailey |
| 2018/0120948 A1 | 5/2018 | Aleem et al. |
| 2018/0140441 A1 | 5/2018 | Poirters |
| 2018/0150033 A1 | 5/2018 | Lake et al. |
| 2018/0153430 A1 | 6/2018 | Ang et al. |

(56) References Cited

U.S. PATENT DOCUMENTS

| | | | |
|---|---|---|---|
| 2018/0153444 A1 | 6/2018 | Yang et al. | |
| 2018/0154140 A1 | 6/2018 | Bouton et al. | |
| 2018/0178008 A1 | 6/2018 | Bouton et al. | |
| 2018/0217249 A1* | 8/2018 | La Salla | G06K 9/00664 |
| 2018/0301057 A1 | 10/2018 | Hargrove et al. | |
| 2018/0307314 A1 | 10/2018 | Connor | |
| 2018/0321745 A1 | 11/2018 | Morun et al. | |
| 2018/0321746 A1 | 11/2018 | Morun et al. | |
| 2018/0333575 A1 | 11/2018 | Bouton | |
| 2018/0344195 A1 | 12/2018 | Morun et al. | |
| 2018/0356890 A1* | 12/2018 | Zhang | A61H 23/0236 |
| 2018/0360379 A1 | 12/2018 | Harrison et al. | |
| 2019/0008453 A1 | 1/2019 | Spoof | |
| 2019/0025919 A1 | 1/2019 | Tadi et al. | |
| 2019/0033967 A1 | 1/2019 | Morun et al. | |
| 2019/0033974 A1 | 1/2019 | Mu et al. | |
| 2019/0038166 A1 | 2/2019 | Tavabi et al. | |
| 2019/0076716 A1 | 3/2019 | Chiou et al. | |
| 2019/0121305 A1 | 4/2019 | Kaifosh et al. | |
| 2019/0121306 A1 | 4/2019 | Kaifosh et al. | |
| 2019/0150777 A1 | 5/2019 | Guo et al. | |
| 2019/0192037 A1 | 6/2019 | Morun et al. | |
| 2019/0212817 A1 | 7/2019 | Kaifosh et al. | |
| 2019/0223748 A1 | 7/2019 | Al-natsheh et al. | |
| 2019/0227627 A1 | 7/2019 | Kaifosh et al. | |
| 2019/0228330 A1 | 7/2019 | Kaifosh et al. | |
| 2019/0228533 A1 | 7/2019 | Giurgica-Tiron et al. | |
| 2019/0228579 A1 | 7/2019 | Kaifosh et al. | |
| 2019/0228590 A1 | 7/2019 | Kaifosh et al. | |
| 2019/0228591 A1 | 7/2019 | Giurgica-Tiron et al. | |
| 2019/0247650 A1 | 8/2019 | Tran | |
| 2019/0279407 A1* | 9/2019 | McHugh | G06F 3/0482 |
| 2019/0357787 A1 | 11/2019 | Barachant et al. | |
| 2019/0362557 A1 | 11/2019 | Lacey et al. | |

FOREIGN PATENT DOCUMENTS

| | | |
|---|---|---|
| CA | 2939644 A1 | 8/2015 |
| CN | 1838933 A | 9/2006 |
| CN | 103777752 A | 5/2014 |
| CN | 105190578 A | 12/2015 |
| CN | 106102504 A | 11/2016 |
| EP | 2198521 B1 | 6/2012 |
| EP | 2959394 A1 | 12/2015 |
| EP | 3104737 A1 | 12/2016 |
| JP | H05-277080 A | 10/1993 |
| JP | 2005-095561 A | 4/2005 |
| JP | 2010-520561 A | 6/2010 |
| JP | 2016-507851 A | 3/2016 |
| JP | 2017-509386 A | 4/2017 |
| KR | 2015-0123254 A | 11/2015 |
| KR | 2016-0121552 A | 10/2016 |
| KR | 10-1790147 B1 | 10/2017 |
| WO | WO 2008/109248 A2 | 9/2008 |
| WO | WO 2009/042313 A1 | 4/2009 |
| WO | WO 2010/104879 A2 | 9/2010 |
| WO | WO 2012/155157 A1 | 11/2012 |
| WO | WO 2014/130871 A1 | 8/2014 |
| WO | WO 2014/186370 A1 | 11/2014 |
| WO | WO 2014/194257 A1 | 12/2014 |
| WO | WO 2014/197443 A1 | 12/2014 |
| WO | WO 2015/027089 A1 | 2/2015 |
| WO | WO 2015/073713 A1 | 5/2015 |
| WO | WO 2015/081113 A1 | 6/2015 |
| WO | WO 2015/123445 A1 | 8/2015 |
| WO | 2015/192117 A1 | 12/2015 |
| WO | WO 2015/199747 A1 | 12/2015 |
| WO | WO 2016/041088 A1 | 3/2016 |
| WO | WO 2017/062544 A1 | 4/2017 |
| WO | WO 2017/092225 A1 | 6/2017 |
| WO | WO 2017/120669 A1 | 7/2017 |
| WO | WO 2017/172185 A1 | 10/2017 |
| WO | WO 2017/208167 A1 | 12/2017 |
| WO | 2018/098046 A2 | 5/2018 |
| WO | 2020/072915 A1 | 4/2020 |

OTHER PUBLICATIONS

Extended European Search Report for European Application No. EP 17835140.9 dated Nov. 26, 2019.
International Preliminary Report on Patentability for International Application No. PCT/US2017/043686 dated Feb. 7, 2019.
International Search Report and Written Opinion for International Application No. PCT/US2017/043686 dated Oct. 6, 2017.
International Preliminary Report on Patentability for International Application No. PCT/US2017/043693 dated Feb. 7, 2019.
International Search Report and Written Opinion for International Application No. PCT/US2017/043693 dated Oct. 6, 2017.
International Preliminary Report on Patentability for International Application No. PCT/US2017/043791 dated Feb. 7, 2019.
International Search Report and Written Opinion for International Application No. PCT/US2017/043791 dated Oct. 5, 2017.
International Preliminary Report on Patentability for International Application No. PCT/US2017/043792 dated Feb. 7, 2019.
International Search Report and Written Opinion for International Application No. PCT/US2017/043792 dated Oct. 5, 2017.
International Search Report and Written Opinion for International Application No. PCT/US2018/056768 dated Jan. 15, 2019.
International Search Report and Written Opinion for International Application No. PCT/US2018/061409 dated Mar. 12, 2019.
International Search Report and Written Opinion for International Application No. PCT/US2018/063215 dated Mar. 21, 2019.
International Search Report and Written Opinion for International Application No. PCT/US2019/015134 dated May 15, 2019.
International Search Report and Written Opinion for International Application No. PCT/US2019/015167 dated May 21, 2019.
International Search Report and Written Opinion for International Application No. PCT/US2019/015174 dated May 21, 2019.
International Search Report and Written Opinion for International Application No. PCT/US2019/015238 dated May 16, 2019.
International Search Report and Written Opinion for International Application No. PCT/US2019/015183 dated May 3, 2019.
International Search Report and Written Opinion for International Application No. PCT/US2019/015180 dated May 28, 2019.
International Search Report and Written Opinion for International Application No. PCT/US2019/015244 dated May 16, 2019.
International Search Report and Written Opinion for International Application No. PCT/US2019/037302 dated Oct. 11, 2019.
International Search Report and Written Opinion for International Application No. PCT/US2019/028299 dated Aug. 9, 2019.
International Search Report and Written Opinion for International Application No. PCT/US2019/034173 dated Sep. 18, 2019.
International Search Report and Written Opinion for International Application No. PCT/US2019/042579 dated Oct. 31, 2019.
Invitation to Pay Additional Fees for International Application No. PCT/US2019/031114 dated Aug. 6, 2019.
Invitation to Pay Additional Fees for International Application No. PCT/US2019/049094 dated Oct. 24, 2019.
International Search Report and Written Opinion for International Application No. PCT/US2019/052131 dated Dec. 6, 2019.
International Search Report and Written Opinion for International Application No. PCT/US2019/046351 dated Nov. 7, 2019.
International Search Report and Written Opinion for International Application No. PCT/US19/20065 dated May 16, 2019.
Al-Mashhadany, Inverse Kinematics Problem (IKP) of 6-DOF Manipulator Bgy Locally Recurrent Neural Networks (LRNNs). Management and Service Science (MASS). 2010 International Conference ON, IEEE. Aug. 24, 2010. 5 pages. ISBN: 978-1-4244-5325-2.
Arkenbout et al., Robust Hand Motion Tracking through Data Fusion of 5DT Data Glove and Nimble VR Kinect Camera Measurements. Sensors. 2015;15:31644-71.
Benko et al., Enhancing Input On and Above the Interactive Surface with Muscle Sensing. The ACM International Conference on Interactive Tabletops and Surfaces. ITS '09. 2009:93-100.
Boyali et al., Spectral Collaborative Representation based Classification for hand gestures recognition on electromyography signals. Biomedical Signal Processing and Control. 2016;24:11-18.

(56) References Cited

OTHER PUBLICATIONS

Cheng et al., A Novel Phonology- and Radical-Coded Chinese Sign Language Recognition Framework Using Accelerometer and Surface Electromyography Sensors. Sensors. 2015;15:23303-24.
Csapo et al., Evaluation of Human-Myo Gesture Control Capabilities in Continuous Search and Select Operations. 7th IEEE International Conference on Cognitive Infocommunications. 2016;000415-20.
Davoodi et al., Development of a Physics-Based Target Shooting Game to Train Amputee Users of Multijoint Upper Limb Prostheses. Presence. Massachusetts Institute of Technology. 2012;21(1):85-95.
Delis et al., Development of a Myoelectric Controller Based on Knee Angle Estimation. Biodevices 2009. International Conference on Biomedical Electronics and Devices. Jan. 17, 2009. 7 pages.
Diener et al., Direct conversion from facial myoelectric signals to speech using Deep Neural Networks. 2015 International Joint Conference on Neural Networks (IJCNN). Oct. 1, 2015. 7 pages.
Ding et al., HMM with improved feature extraction-based feature parameters for identity recognition of gesture command operators by using a sensed Kinect-data stream. Neurocomputing. 2017;262:108-19.
Farina et al., Man/machine interface based on the discharge timings of spinal motor neurons after targeted muscle reinnervation. Nature. Biomedical Engineering. 2017;1:1-12.
Favorskaya et al., Localization and Recognition of Dynamic Hand Gestures Based on Hierarchy of Manifold Classifiers. International Archives of the Photogrammetry, Remote Sensing and Spatial Information Sciences. 2015;XL-5/W6:1-8.
Gallina et al., Surface EMG Biofeedback. Surface Electromyography: Physiology, Engineering, and Applications. 2016:485-500.
Gopura et al., A Human Forearm and wrist motion assist exoskeleton robot with EMG-based fuzzy-neuro control. Proceedings of the 2nd IEEE/RAS-EMBS International Conference on Biomedical Robotics and Biomechatronics. Oct. 19-22, 2008. 6 pages.
Hauschild et al., A Virtual Reality Environment for Designing and Fitting Neural Prosthetic Limbs. IEEE Transactions on Neural Systems and Rehabilitation Engineering. 2007;15(1):9-15.
Jiang, Purdue University Graduate School Thesis/Dissertation Acceptance. Graduate School Form 30. Updated Jan. 15, 2015. 24 pages.
Kawaguchi et al., Estimation of Finger Joint Angles Based on Electromechanical Sensing of Wrist Shape. IEEE Transactions on Neural Systems and Rehabilitation Engineering. 2017;25(9):1409-18.
Kim et al., Real-Time Human Pose Estimation and Gesture Recognition from Depth Images Using Superpixels and SVM Classifier. Sensors. 2015;15:12410-27.
Kipke et al., Silicon-substrate Intracortical Microelectrode Arrays for Long-Term Recording of Neuronal Spike Activity in Cerebral Cortex. IEEE Transactions on Neural Systems and Rehabilitation Engineering. 2003;11(2):151-155.
Koerner, Design and Characterization of the Exo-Skin Haptic Device: A Novel Tendon Actuated Textile Hand Exoskeleton. 2017. 5 pages.
Lee et al., Motion and Force Estimation System of Human Fingers. Journal of Institute of Control, Robotics and Systems. 2011;17(10):1014-1020.
Li et al., Motor Function Evaluation of Hemiplegic Upper-Extremities Using Data Fusion from Wearable Inertial and Surface EMG Sensors. Sensors. MDPI. 2017;17(582):1-17.
Lopes et al., Hand/arm gesture segmentation by motion using IMU and EMG sensing. ScienceDirect. Elsevier. Procedia Manufacturing. 2017;11:107-13.
Marcard et al., Sparse Inertial Poser: Automatic 3D Human Pose Estimation from Sparse IMUs. Eurographics. 2017;36(2). 12 pages.
Martin et al., A Novel Approach of Prosthetic Arm Control using Computer Vision, Biosignals, and Motion Capture. IEEE. 2014. 5 pages.
Mcintee, A Task Model of Free-Space Movement-Based Gestures. Dissertation. Graduate Faculty of North Carolina State University. Computer Science. 2016. 129 pages.
Mendes et al., Sensor Fusion and Smart Sensor in Sports and Biomedical Applications. Sensors. 2016;16(1569):1-31.
Mohamed, Homogeneous cognitive based biometrics for static authentication. Dissertation submitted to University of Victoria, Canada. 2010. 149 pages. URL:http://hdl.handle.net/1828/3211 [last accessed Oct. 11, 2019].
Naik et al., Source Separation and Identification issues in bio signals: A solution using Blind source separation. Intech. 2009. 23 pages.
Naik et al., Subtle Hand gesture identification for HCI using Temporal Decorrelation Source Separation BSS of surface EMG. Digital Image Computing Techniques and Applications. IEEE Computer Society. 2007;30-7.
Negro et al., Multi-channel intramuscular and surface EMG decomposition by convolutive blind source separation. Journal of Neural Engineering. 2016;13:1-17.
Saponas et al., Demonstrating the Feasibility of Using Forearm Electromyography for Muscle-Computer Interfaces. CHI 2008 Proceedings. Physiological Sensing for Input. 2008:515-24.
Saponas et al., Enabling Always-Available Input with Muscle-Computer Interfaces. UIST'09. 2009:167-76.
Saponas et al., Making Muscle-Computer Interfaces More Practical. CHI 2010: Brauns and Brawn. 2010:851-4.
Sartori et al., Neural Data-Driven Musculoskeletal Modeling for Personalized Neurorehabilitation Technologies. IEEE Transactions on Biomedical Engineering. 2016;63(5):879-93.
Sauras-Perez et al., A Voice and Pointing Gesture Interaction System for Supporting Human Spontaneous Decisions in Autonomous Cars. Clemson University. All Dissertations. 2017. 174 pages.
Shen et al., I am a Smartwatch and I can Track my User's Arm. University of Illinois at Urbana-Champaign. MobiSys' 16. 12 pages.
Son et al., Evaluating the utility of two gestural discomfort evaluation methods. PLOS One. 2017. 21 pages.
Strbac et al., Microsoft Kinect-Based Artificial Perception System for Control of Functional Electrical Stimulation Assisted Grasping. Hindawi Publishing Corporation. BioMed Research International. 2014. 13 pages.
Torres, Myo Gesture Control Armband. PCMag. Https://www.pcmag.com/article2/0,2817,2485462,00.asp 2015. 9 pages.
Valero-Cuevas et al., Computational Models for Neuromuscular Function. NIH Public Access Author Manuscript. Jun. 16, 2011. 52 pages.
Wittevrongel et al., Spatiotemporal Beamforming: A Transparent and Unified Decoding Approach to Synchronous Visual Brain-Computer Interfacing. Frontiers in Neuroscience. 2017;11:1-12.
Wodzinski et al., Sequential Classification of Palm Gestures Based on A* Algorithm and MLP Neural Network for Quadrocopter Control. Metrol. Meas. Syst., 2017;24(2):265-76.
Xue et al., Multiple Sensors Based Hand Motion Recognition Using Adaptive Directed Acyclic Graph. Applied Sciences. MDPI. 2017;7(358):1-14.
Yang et al., Surface EMG based handgrip force predictions using gene expression programming. Neurocomputing. 2016;207:568-579.
Zacharaki et al., Spike pattern recognition by supervised classification in low dimensional embedding space. Brain Informatics. 2016;3:73-8. DOI: 10.1007/s40708-016-0044-4.
EP 17835111.0, Nov. 21, 2019, Extended European Search Report.
EP 17835140.9, Nov. 26, 2019, Extended European Search Report.
PCT/US19/20065, May 16, 2019, International Search Report and Written Opinion.
PCT/US2017/043686, Oct. 6, 2017, International Search Report and Written Opinion.
PCT/US2017/043686, Feb. 7, 2019, International Preliminary Report on Patentability.
PCT/US2017/043693, Oct. 6, 2017, International Search Report and Written Opinion.
PCT/US2017/043693, Feb. 7, 2019, International Preliminary Report on Patentability.
PCT/US2017/043791, Oct. 5, 2017, International Search Report and Written Opinion.

(56) References Cited

OTHER PUBLICATIONS

PCT/US2017/043791, Feb. 7, 2019, International Preliminary Report on Patentability.
PCT/US2017/043792, Oct. 5, 2017, International Search Report and Written Opinion.
PCT/US2017/043792, Feb. 7, 2019, International Preliminary Report on Patentability.
PCT/US2018/056768, Jan. 15, 2019, International Search Report and Written Opinion.
PCT/US2018/061409, Mar. 12, 2019, International Search Report and Written Opinion.
PCT/US2018/063215, Mar. 21, 2019, International Search Report and Written Opinion.
PCT/US2019/015134, May 15, 2019, International Search Report and Written Opinion.
PCT/US2019/015167, May 21, 2019, International Search Report and Written Opinion.
PCT/US2019/015174, May 21, 2019, International Search Report and Written Opinion.
PCT/US2019/015180, May 28, 2019, International Search Report and Written Opinion.
PCT/US2019/015183, May 3, 2019, International Search Report and Written Opinion.
PCT/US2019/015238, May 16, 2019, International Search Report and Written Opinion.
PCT/US2019/015244, May 16, 2019, International Search Report and Written Opinion.
PCT/US2019/028299, Aug. 9, 2019, International Search Report and Written Opinion.
PCT/US2019/031114, Aug. 6, 2019, Invitation to Pay Additional Fees.
PCT/US2019/034173, Sep. 18, 2019, International Search Report and Written Opinion.
PCT/US2019/037302, Oct. 11, 2019, International Search Report and Written Opinion.
PCT/US2019/042579, Oct. 31, 2019, International Search Report and Written Opinion.
PCT/US2019/046351, Nov. 7, 2019, International Search Report and Written Opinion.
PCT/US2019/049094, Oct. 24, 2019, Invitation to Pay Additional Fees.
PCT/US2019/052131, Dec. 6, 2019, International Search Report and Written Opinion.
International Search Report and Written Opinion received for PCT Application Serial No. PCT/US2019/054716 dated Dec. 20, 2019, 21 pages.

* cited by examiner

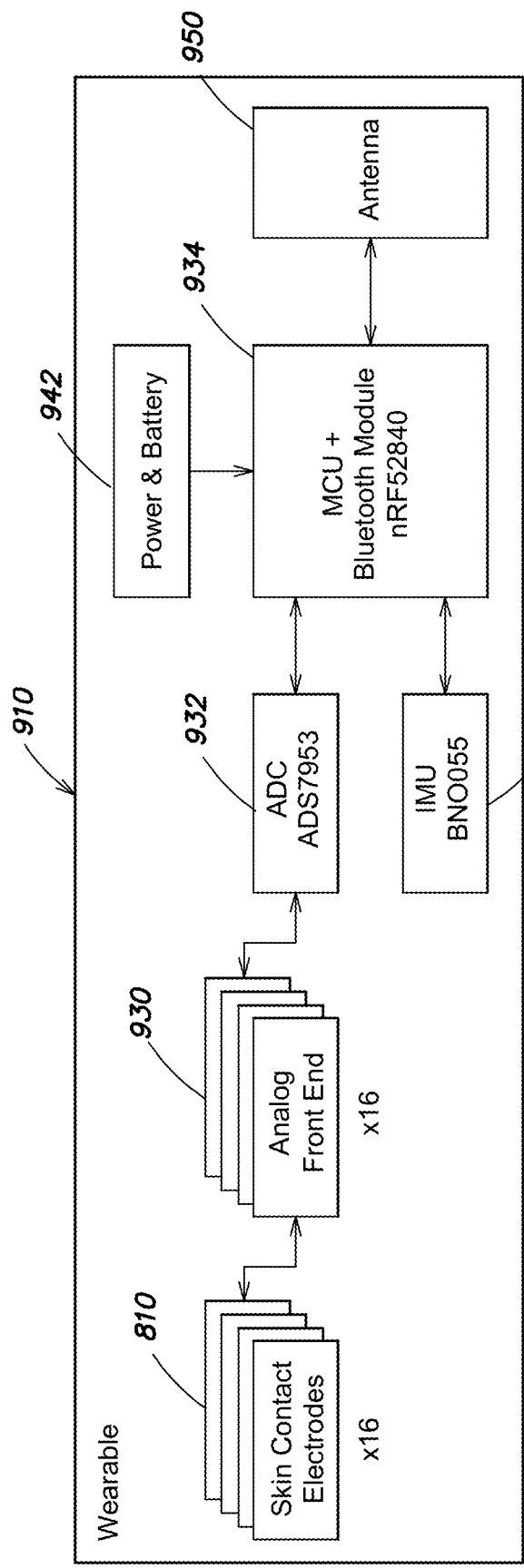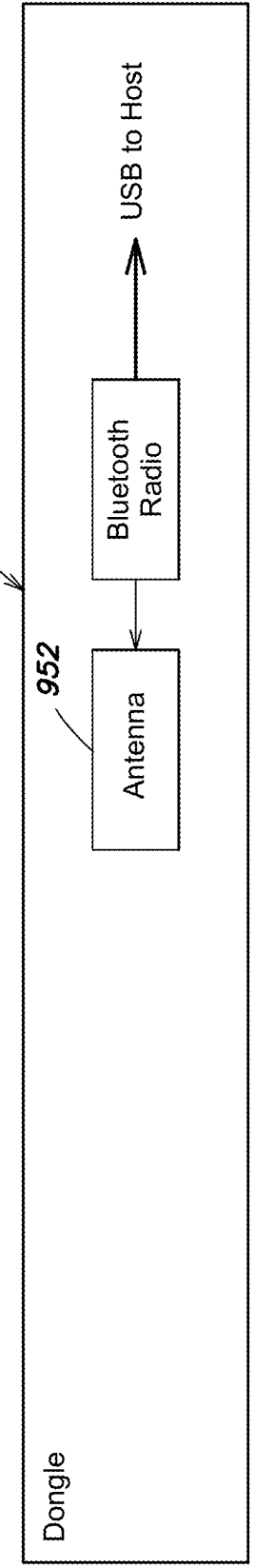
FIG. 9A
FIG. 9B

USE OF NEUROMUSCULAR SIGNALS TO PROVIDE ENHANCED INTERACTIONS WITH PHYSICAL OBJECTS IN AN AUGMENTED REALITY ENVIRONMENT

CROSS-REFERENCE TO RELATED APPLICATIONS

This application claims the benefit under 35 U.S.C. § 119(e) of U.S. Provisional Patent Application Ser. No. 62/741,781, filed Oct. 5, 2018, entitled "USE OF NEUROMUSCULAR SIGNALS TO PROVIDE ENHANCED INTERACTIONS WITH PHYSICAL OBJECTS IN AN AUGMENTED REALITY ENVIRONMENT," the entire contents of which is incorporated by reference herein.

FIELD OF THE INVENTION

The present technology relates to systems and methods that detect and interpret neuromuscular signals for use in performing actions in an augmented reality (AR) environment as well as other types of extended reality (XR) environments, such as a virtual reality (VR) environment, a mixed reality (MR) environment, and the like.

BACKGROUND

AR systems provide users with an interactive experience of a real-world environment supplemented with virtual information by overlaying computer-generated perceptual or virtual information on aspects of the real-world environment. Various techniques exist for controlling operations of an AR system. Typically, one or more input devices, such as a controller, a keyboard, a mouse, a camera, a microphone, and the like, may be used to control operations of the AR system. Physical objects in the real-world environment may be annotated with visual indicators within an AR environment generated by the AR system. The visual indicators may provide a user of the AR system with information about the physical objects.

SUMMARY

According to aspects of the technology described herein, a computerized system for interacting with a physical object in an augmented reality (AR) environment generated by an AR system is provided. The computerized system may comprise: a plurality of neuromuscular sensors configured to sense a plurality of neuromuscular signals from a user, and at least one computer processor. The plurality of neuromuscular sensors may be arranged on one or more wearable devices worn by the user to sense the plurality of neuromuscular signals. The at least one computer processor may be programmed to: determine, based at least in part, on the plurality of neuromuscular signals sensed by the plurality of neuromuscular sensors, information relating to an interaction of the user with the physical object in the AR environment generated by the AR system; and instruct the AR system to provide feedback based, at least in part, on the information relating to the interaction of the user with the physical object.

In an aspect, the at least one computer processor may be further programmed to instruct the AR system to display at least one visual indicator on the physical object in the AR environment.

In a variation of this aspect, the at least one computer processor may determine the information relating to the interaction of the user with the physical object based, at least in part, on an interaction of the user with the at least one visual indicator displayed on the physical object.

In an aspect, the computerized system may further comprise at least one camera arranged to capture at least one image of at least a part of the user, or at least a part of the physical object, or at least a part of the user and at least a part of the physical object. The at least one computer processor may determine the information relating to the interaction of the user with the physical object based, at least in part, on the at least one image.

In another aspect, the at least one computer processor may instruct the AR system to provide the feedback to the user.

In variations of this aspect, the at least one computer processor may instruct the AR system to provide the feedback as visual feedback to the user within the AR environment. In one example, the at least one processor may instruct the AR system to provide the visual feedback to the user within the AR environment as a change in at least one property of at least one visual indicator displayed by the AR system. In another example, the at least one processor may instruct the AR system to provide the visual feedback to the user within the AR environment as a display of at least one new visual indicator associated with the physical object within the AR environment.

In another variation of this aspect, the at least one processor may instruct the AR system to provide the feedback to the user as audio feedback, or electrical stimulation feedback, or audio feedback and electrical stimulation feedback.

In further variations of this aspect, the feedback provided to the user may comprise an indication of an amount of force applied to the physical object by the user. The amount of force may be determined based, at least in part, on the plurality of neuromuscular signals. In one example, the computerized system may further comprise at least one camera arranged to capture at least one image; the amount of force applied to the physical object may be determined based, at least in part, on the at least one image.

In an aspect, the at least one computer processor may instruct the AR system to provide the feedback as a change in at least one function of the physical object when the at least one function is used within the AR environment.

In another aspect, the at least one computer processor may instruct the AR system to provide the feedback to a different user other than the user interacting with the physical object.

In a variation of this aspect, the feedback may be provided to the different user within an AR environment experienced by the different user.

In an aspect, the computerized system may further comprise haptic circuitry arranged to deliver haptic signals to the user. The haptic circuitry may be arranged on a wearable device worn by the user. The at least one computer processor may be programmed to instruct the AR system or a controller external to the AR system to provide feedback to the user as haptic feedback delivered via the haptic circuitry.

In variations of this aspect, the haptic circuitry may comprise any one or any combination of: a vibration actuator, a skin-tap actuator, a low-voltage electrical-jolt stimulation circuit, and a force actuator.

In another variation of this aspect, the wearable device on which the haptic circuitry is arranged may comprise a wearable patch.

In another variation of this aspect, the haptic circuitry may be arranged on the one or more wearable devices on which the plurality of neuromuscular sensors are arranged.

In another aspect, the information relating to the interaction of the user with the physical object may comprise information that the user has interacted with a particular physical object. The at least one computer processor may instruct the AR system to provide the feedback as a modification of at least one interaction property of the particular physical object, and as an indication of the modification to the user.

In variations of this aspect, the modification of the at least one interaction property of the particular physical object may comprise an enablement of at least one virtual control associated with the particular physical object. In a further variation, the at least one computer processor may be programmed to disable the at least one virtual control associated with the particular physical object in response to receiving input from the user. In a further variation, the at least one virtual control associated with the particular physical object may be disabled by the at least one computer processor based, at least in part, on the plurality of neuromuscular signals.

In other variations of this aspect, the particular physical object may comprise a writing implement. The modification of the at least one interaction property may comprise activation of a set of augmented features for the writing implement. In one example, the set of augmented features may include features that enable the user to interact with the writing implement in one or more ways to change one or more writing characteristics of the writing implement in the AR environment. In another example, the at least one computer processor may be programmed to: determine, based at least in part on the plurality of neuromuscular signals, that the user is interacting with the writing implement in one of the one or more ways; and change a corresponding writing characteristic of the writing implement in response to a determination that the user is interacting with the writing implement in the one of the one or more ways. The one or more writing characteristics may comprise any one or any combination of: a writing color, a line thickness, a brush shape, a drawing mode, and an erasing mode.

In an aspect, functions of the physical object in the AR environment may be controlled by a set of virtual controls. The at least one processor may be programmed to instruct the AR system, based at least in part on the plurality of neuromuscular signals, to perform any one or any combination of: an activation of the set of virtual controls, a deactivation of the set of virtual controls, and a modification of the set of virtual controls.

In a variation of this aspect, the plurality of neuromuscular signals may comprise signals arising from a gesture performed by the user. The gesture may comprise any one or any combination of: a static gesture, a dynamic gesture, a covert gesture, a muscular activation state, and a sub-muscular activation state.

In another aspect, the AR environment may include a plurality of physical objects. Each of the plurality of physical objects may be associated with a set of control actions, and the at least one computer processor may be programmed to: identify the physical object with which the user is interacting within the AR environment, and activate a corresponding set of control actions associated with the identified physical object.

In a variation of this aspect, the feedback may comprise a visual display within the AR environment. The visual display may indicate the activated set of control actions.

In another variation of this aspect, the computerized system may further comprise at least one camera arranged to capture at least one image. The at least one computer processor may identify the physical object with which the user is interacting within the AR environment, from amongst the plurality of physical objects in the AR environment, based, at least in part, on the at least one image captured by the at least one camera. The at least one computer processor may be programmed to identify that the user is interacting with the identified physical object based, at least in part, on the plurality of neuromuscular signals.

In another variation of this aspect, the at least one computer processor may be programmed to determine the information relating to the interaction of the user with the physical object based, at least in part, on the activated set of control actions.

In another variation of this aspect, the at least one computer processor may determine the information relating to the interaction of the user with the physical object based, at least in part, on an output of an inference model to which the plurality of neuromuscular signals, or information derived from the plurality of neuromuscular signals, or the plurality of neuromuscular signals and the information derived from the plurality of neuromuscular signals are provided as input. Prior to the output of the inference model being rendered, the at least one computer processor may provide to the inference model information about the identified physical object, or information associated with the activated set of control actions, or the information about the identified physical object and the information associated with the activated set of control actions.

In an aspect, the AR environment may include a plurality of physical objects. Each of the plurality of physical objects may be associated with a set of control actions. The at least one computer processor may be programmed to instruct the AR system to: select a particular physical object of the plurality of physical objects for active control in the AR environment, based at least in part on the plurality of neuromuscular signals; and activate a corresponding set of control actions associated with the particular physical object.

In a variation of this aspect, the plurality of neuromuscular signals may comprise signals arising from a gesture performed by the user. The gesture may comprise any one or any combination of: a static gesture, a dynamic gesture, a covert gesture, a muscular activation state, and a sub-muscular activation state.

In another aspect, the at least one computer processor may be programmed to modify an operation of the AR system based, at least in part, on the information relating to the interaction of the user with the physical object.

In a variation of this aspect, the at least one computer processor may modify the operation of the AR system by instructing the AR system to enter a higher-precision mode for detecting finer-grained interactions of the user with the physical object. In an example, when in the higher-precision mode, the AR system may use a greater weight for the plurality of neuromuscular signals than a weight used for auxiliary signals from at least one auxiliary sensor, to determine the information relating to the interaction of the user with the physical object.

According to aspects of the technology described herein, a method is provided in which is performed by a computerized system for enabling a user to interact with a physical object in an augmented reality (AR) environment generated by an AR system based, at least in part, on neuromuscular signals. The method may comprise: obtaining a plurality of neuromuscular signals from a user using a plurality of neuromuscular sensors arranged on one or more wearable devices worn by the user to sense the plurality of neuromuscular signals; determining, using at least one computer processor coupled to a memory storing code executed by the at least one computer processor, based at least in part on the plurality of neuromuscular signals, information relating to an interaction of the user with the physical object in the AR environment generated by the AR system; and instructing, using the at least one computer processor, the AR system to provide feedback based, at least in part, on the information relating to the interaction of the user with the physical object.

In an aspect, the method may further comprise instructing, using the at least one computer processor, the AR system to display at least one visual indicator on the physical object in the AR environment.

In a variation of this aspect, the determining of the information relating to the interaction of the user with the physical object may be based, at least in part, on an interaction of the user with the at least one visual indicator displayed on the physical object.

In another aspect, the method may further comprise capturing, using at least one camera, at least one image of at least a part of the user, or at least a part of the physical object, or at least a part of the user and at least a part of the physical object. The determining of the information relating to the interaction of the user with the physical object may be based, at least in part, on the at least one image.

In an aspect, the instructing may instruct the AR system to provide the feedback to the user.

In variations of this aspect, the instructing may instruct the AR system to provide the feedback as visual feedback to the user within the AR environment. In one example, the instructing may instruct the AR system to provide the visual feedback to the user within the AR environment as a change in at least one property of at least one visual indicator displayed by the AR system. In another example, the visual feedback is provided to the user within the AR environment as a display of at least one new visual indicator associated with the physical object within the AR environment.

In another variation, the instructing may instruct the AR system to provide the feedback to the user as audio feedback, or electrical stimulation feedback, or audio feedback and electrical stimulation feedback.

In another variation, the feedback provided to the user may comprise an indication of an amount of force applied to the physical object by the user. The amount of force may be determined based, at least in part, on the plurality of neuromuscular signals. In one example, the method may further comprise capturing, using at least one camera, at least one image; the amount of force applied to the physical object may be determined based, at least in part, on the at least one image.

In another aspect, the instructing may instruct the AR system to provide the feedback as a change in at least one function of the physical object when the at least one function is used within the AR environment.

In an aspect, the instructing may instruct the AR system to provide the feedback to a different user other than the user interacting with the physical object.

In a variation of this aspect, the feedback may be provided to the different user within an AR environment experienced by the different user.

In another aspect, the method may further comprise instructing, using the at least one computer processor, the AR system or a controller external to the AR system to provide feedback to the user as haptic feedback delivered via haptic circuitry arranged to deliver haptic signals to the user. The haptic circuitry may be arranged on a wearable device worn by the user.

In a variation of this aspect, the haptic circuitry may comprise any one or any combination of: a vibration actuator, a skin-tap actuator, a low-voltage electrical-jolt stimulation circuit, and a force actuator.

In another variation of this aspect, the wearable device on which the haptic circuitry is arranged may comprise a wearable patch.

In another variation, the haptic circuitry may be arranged on the one or more wearable devices on which the plurality of neuromuscular sensors are arranged.

In an aspect, the information relating to the interaction of the user with the physical object may comprise information that the user has interacted with a particular physical object. The instructing may instruct the AR system to provide the feedback as a modification of at least one interaction property of the particular physical object, and as an indication of the modification to the user.

In a variation of this aspect, the modification of the at least one interaction property of the particular physical object may comprise an enablement of at least one virtual control associated with the particular physical object. In a further variation, the method may further comprise disabling, by the at least one computer processor, the at least one virtual control associated with the particular physical object in response to input from the user. In one example, the at least one virtual control associated with the particular physical object may be disabled by the at least one computer processor based, at least in part, on the plurality of neuromuscular signals.

In another variation of this aspect, the particular physical object may comprise a writing implement. The modification of the at least one interaction property may comprise activation of a set of augmented features for the writing implement. In one example, the set of augmented features may include features that enable the user to interact with the writing implement in one or more ways to change one or more writing characteristics of the writing implement in the AR environment. In a further variation, the method may further comprise: determining, by the at least one computer processor based at least in part on the plurality of neuromuscular signals, that the user is interacting with the writing implement in one of the one or more ways; and changing, by the at least one computer processor, a corresponding writing characteristic of the writing implement in response to a determination that the user is interacting with the writing implement in the one of the one or more ways. The one or more writing characteristics may comprise any one or any combination of: a writing color, a line thickness, a brush shape, a drawing mode, and an erasing mode.

In another aspect, functions of the physical object in the AR environment may be controlled by a set of virtual controls control. The method may further comprise instructing the AR system, using the at least one computer processor, based at least in part on the plurality of neuromuscular signals, to perform any one or any combination of: an activation of the set of virtual controls, a deactivation of the set of virtual controls, and a modification of the set of virtual controls.

In a variation of this aspect, the plurality of neuromuscular signals may comprise signals arising from a gesture performed by the user. The gesture may comprise any one or any combination of: a static gesture, a dynamic gesture, a covert gesture, a muscular activation state, and a submuscular activation state.

In an aspect, the AR environment may include a plurality of physical objects. Each of the plurality of physical objects may be associated with a set of control actions. The method may further comprise: identifying, by the at least one computer processor, the physical object with which the user is interacting within the AR environment; and activating, by the at least one computer processor, a corresponding set of control actions associated with the identified physical object.

In a variation of this aspect, the feedback may comprise a visual display within the AR environment. The visual display may indicate the activated set of control actions.

In another variation of this aspect, the method may further comprise capturing, using at least one camera, at least one image. The identifying may identify the physical object from amongst the plurality of physical objects in the AR environment based, at least in part, on the at least one image captured by the at least one camera. The at least one computer processor may identify that the user is interacting with the identified physical object based, at least in part, on the plurality of neuromuscular signals.

In another variation of this aspect, the determining of the information relating to the interaction of the user with the physical object may be based, at least in part, on the activated set of control actions.

In another variation of this aspect, the determining of the information relating to the interaction of the user with the physical object may be based, at least in part, on an output of an inference model to which the plurality of neuromuscular signals, or information derived from the plurality of neuromuscular signals, or the plurality of neuromuscular signals and the information derived from the plurality of neuromuscular signals are provided as input. The method may further comprise, prior to the output of the inference model being rendered, providing to the inference model information about the identified physical object, or information associated with the activated set of control actions, or the information about the identified physical object and the information associated with the activated set of control actions.

In another aspect, the AR environment may include a plurality of physical objects. Each of the plurality of physical objects may be associated with a set of control actions. The method may further comprise instructing, using the at least one computer processor, the AR system to: select a particular physical object of the plurality of physical objects for active control in the AR environment, based at least in part on the plurality of neuromuscular signals; and activate a corresponding set of control actions associated with the particular physical object.

In a variation of this aspect, the plurality of neuromuscular signals may comprise signals arising from a gesture performed by the user. The gesture may comprise any one or any combination of: a static gesture, a dynamic gesture, a covert gesture, a muscular activation state, and a sub-muscular activation state.

In an aspect, the method may further comprise modifying, by the at least one computer processor, an operation of the AR system based, at least in part, on the information relation to the interaction of the user with the physical object.

In a variation of this aspect, the at least one computer processor may modify the operation of the AR system by instructing the AR system to enter a higher-precision mode for detecting finer-grained interactions of the user with the physical object. In a further variation, when in the higher-precision mode, the AR system may use a greater weight for the plurality of neuromuscular signals than a weight used for auxiliary signals from at least one auxiliary sensor, to determine the information relating to the interaction of the user with the physical object.

According to aspects of the technology described herein, a non-transitory computer-readable medium is provided in which is encoded a plurality of instructions that, when executed by at least one computer processor, causes the at least computer processor to perform a method for enabling a user to interact with a physical object in an augmented reality (AR) environment generated by an AR system based, at least in part, on neuromuscular signals. The method may comprise: receiving, as input, a plurality of neuromuscular signals obtained from a user via a plurality of neuromuscular sensors arranged on one or more wearable devices worn by the user to sense the plurality of neuromuscular signals; determining, based at least in part, on the plurality of neuromuscular signals, information relating to an interaction of the user with the physical object in the AR environment generated by the AR system; and instructing the AR system to provide feedback based, at least in part, on the information relating to the interaction of the user with the physical object.

In an aspect, the method may further comprise instructing the AR system to display at least one visual indicator on the physical object in the AR environment.

In a variation of this aspect, the determining of the information relating to the interaction of the user with the physical object may be based, at least in part, on an interaction of the user with the at least one visual indicator displayed on the physical object.

In another aspect, the method may further comprise receiving, as input from at least one camera, at least one image of at least a part of the user, or at least a part of the physical object, or at least a part of the user and at least a part of the physical object. The determining of the information relating to the interaction of the user with the physical object may be based, at least in part, on the at least one image.

In an aspect, the instructing may instruct the AR system to provide the feedback to the user.

In a variation of this aspect, the instructing may instruct the AR system to provide the feedback as visual feedback to the user within the AR environment. In one example, the instructing may instruct the AR system to provide the visual feedback to the user within the AR environment as a change in at least one property of at least one visual indicator displayed by the AR system. In another example, the visual feedback may be provided to the user within the AR environment as a display of at least one new visual indicator associated with the physical object within the AR environment.

In another variation, the instructing may instruct the AR system to provide the feedback to the user as audio feedback, or electrical stimulation feedback, or audio feedback and electrical stimulation feedback.

In another variation, the feedback provided to the user may comprise an indication of an amount of force applied to the physical object by the user. The amount of force may be determined based, at least in part, on the plurality of neuromuscular signals. In one example, the method may further comprise receiving, as input from at least one camera, at least one image; the amount of force applied to the physical object may be determined based, at least in part, on the at least one image.

In another aspect, the instructing may instruct the AR system to provide the feedback as a change in at least one function of the physical object when the at least one function is used within the AR environment.

In an aspect, the instructing may instruct the AR system to provide the feedback to a different user other than the user interacting with the physical object.

In a variation of this aspect, the feedback may be provided to the different user within an AR environment experienced by the different user.

In another aspect, the method may further comprise instructing the AR system or a controller external to the AR system to provide feedback to the user as haptic feedback delivered via haptic circuitry arranged to deliver haptic signals to the user. The haptic circuitry may be arranged on a wearable device worn by the user.

In a variation of this aspect, the haptic circuitry may comprise any one or any combination of: a vibration actuator, a skin-tap actuator, a low-voltage electrical-jolt stimulation circuit, and a force actuator.

In another variation of this aspect, the wearable device on which the haptic circuitry is arranged may comprise a wearable patch.

In another variation of this aspect, the haptic circuitry may be arranged on the one or more wearable devices on which the plurality of neuromuscular sensors are arranged.

In an aspect, the information relating to the interaction of the user with the physical object may comprise information that the user has interacted with a particular physical object. The instructing may instructs the AR system to provide the feedback as a modification of at least one interaction property of the particular physical object, and as an indication of the modification to the user.

In a variation of this aspect, the modification of the at least one interaction property of the particular physical object may comprise an enablement of at least one virtual control associated with the particular physical object. In a further variation, the method may further comprise disabling the at least one virtual control associated with the particular physical object in response to input from the user. In one example, the at least one virtual control associated with the particular physical object may be disabled by the at least one computer processor based, at least in part, on the plurality of neuromuscular signals.

In another variation of this aspect, the particular physical object may comprise a writing implement. The modification of the at least one interaction property may comprise activation of a set of augmented features for the writing implement. In a further variation, the set of augmented features may include features that enable the user to interact with the writing implement in one or more ways to change one or more writing characteristics of the writing implement in the AR environment. In a further variation, the method may further comprise: determining, based at least in part on the plurality of neuromuscular signals, that the user is interacting with the writing implement in one of the one or more ways; and changing a corresponding writing characteristic of the writing implement in response to a determination that the user is interacting with the writing implement in the one of the one or more ways. The one or more writing characteristics may comprise any one or any combination of: a writing color, a line thickness, a brush shape, a drawing mode, and an erasing mode.

In another aspect, functions of the physical object in the AR environment may be controlled by a set of virtual controls. The method may further comprise instructing the AR system, using the at least one, based at least in part on the plurality of neuromuscular signals, to perform any one or any combination of: an activation of the set of virtual controls, a deactivation of the set of virtual controls, and a modification of the set of virtual controls.

In a variation of this aspect, the plurality of neuromuscular signals may comprise signals arising from a gesture performed by the user. The gesture may comprise any one or any combination of: a static gesture, a dynamic gesture, a covert gesture, a muscular activation state, and a sub-muscular activation state.

In an aspect, the AR environment may include a plurality of physical objects. Each of the plurality of physical objects may be associated with a set of control actions. The method may further comprise: identifying the physical object with which the user is interacting within the AR environment; and activating a corresponding set of control actions associated with the identified physical object.

In a variation of this aspect, the feedback may comprise a visual display within the AR environment. The visual display may indicate the activated set of control actions.

In another variation of this aspect, the method may further comprise capturing, using at least one camera, at least one image. The identifying may identify the physical object from amongst the plurality of physical objects in the AR environment based, at least in part, on the at least one image captured by the at least one camera. The user may be determined to be interacting with the identified physical object based, at least in part, on the plurality of neuromuscular signals.

In another variation of this aspect, the determining of the information relating to the interaction of the user with the physical object may be based, at least in part, on the activated set of control actions.

In another variation of this aspect, the determining of the information relating to the interaction of the user with the physical object may be based, at least in part, on an output of an inference model to which the plurality of neuromuscular signals, or information derived from the plurality of neuromuscular signals, or the plurality of neuromuscular signals and the information derived from the plurality of neuromuscular signals are provided as input. The method may further comprise, prior to the output of the inference model being rendered, providing to the inference model information about the identified physical object, or information associated with the activated set of control actions, or the information about the identified physical object and the information associated with the activated set of control actions.

In another aspect, the AR environment may include a plurality of physical objects. Each of the plurality of physical objects may be associated with a set of control actions. The method may further comprise instructing the AR system to: select a particular physical object of the plurality of physical objects for active control in the AR environment, based at least in part on the plurality of neuromuscular signals; and activate a corresponding set of control actions associated with the particular physical object.

In a variation of this aspect, the plurality of neuromuscular signals may comprise signals arising from a gesture performed by the user. The gesture may comprise any one or any combination of: a static gesture, a dynamic gesture, a covert gesture, a muscular activation state, and a sub-muscular activation state.

In an aspect, the method may further comprise modifying an operation of the AR system based, at least in part, on the information relating to the interaction of the user with the physical object.

In a variation of this aspect, the modifying of the operation of the AR system may comprise instructing the AR system to enter a higher-precision mode for detecting finer-grained interactions of the user with the physical object. In a further variation, when in the higher-precision mode, the AR system may use a greater weight for the plurality of neuromuscular signals than a weight used for auxiliary signals from at least one auxiliary sensor, to determine the information relating to the interaction of the user with the physical object.

According to aspects of the technology described herein, kit for controlling an augmented reality (AR) system is provided. The kit may comprise: a wearable device comprising a plurality of neuromuscular sensors configured to sense a plurality of neuromuscular signals of a user; and a non-transitory computer-readable medium encoded with a plurality of instructions that, when executed by at least one computer processor, causes the at least one computer processor to perform a method for enabling a user to interact with a physical object in an AR environment generated by the AR system. The method may comprise: receiving, as input, the plurality of neuromuscular signals sensed from the user by the plurality of neuromuscular sensors; determining, based at least in part on the plurality of neuromuscular signals, information relating to an interaction of the user with the physical object in the AR environment generated by the AR system; and instructing the AR system to provide feedback based, at least in part, on the information relating to the interaction of the user with the physical object.

In an aspect, the wearable device may comprise a wearable band structured to be worn around a part of the user.

In another aspect, the wearable device may comprise a wearable patch structured to be worn on a part of the user.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

BRIEF DESCRIPTION OF DRAWINGS

Various non-limiting embodiments of the technology will be described with reference to the following figures. It should be appreciated that the figures are not necessarily drawn to scale.

FIGS. 9A and 9B schematically illustrate components of a computer-based system in which some embodiments of the technology described herein are implemented. FIG. 9A illustrates a wearable portion of the computer-based system, and FIG. 9B illustrates a dongle portion connected to a computer, wherein the dongle portion is configured to communicate with the wearable portion;

DETAILED DESCRIPTION

Figure 1:
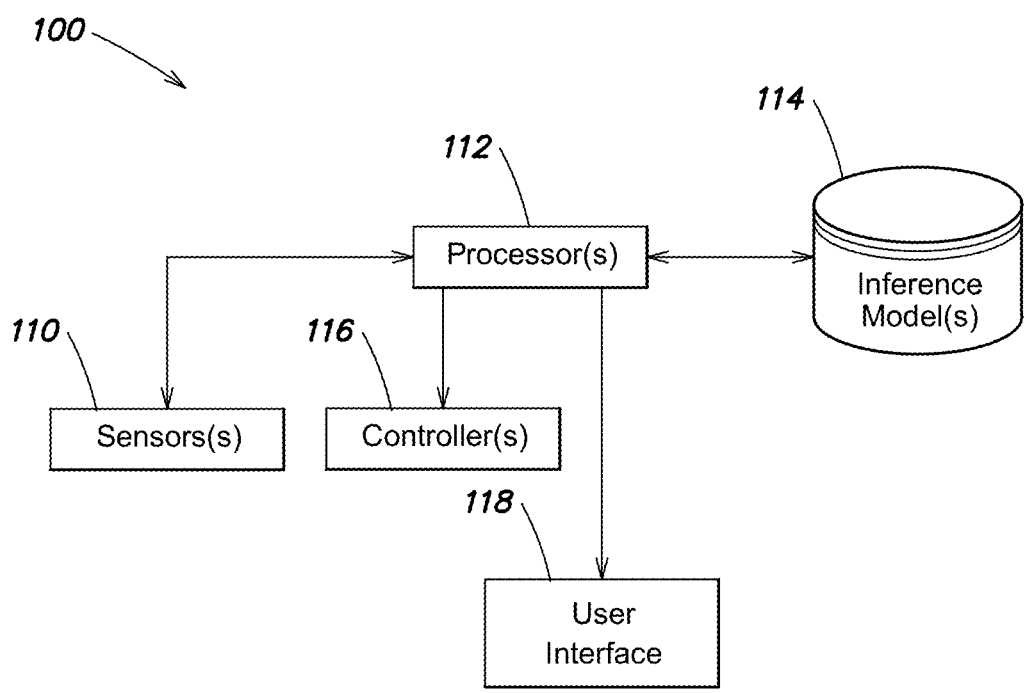
FIG. 1 is a schematic diagram of a computer-based system for processing neuromuscular sensor data, such as signals obtained from neuromuscular sensors, in accordance with some embodiments of the technology described herein.

The inventors have developed novel techniques for controlling AR systems as well as other types of XR systems, such as VR systems and MR systems. Various embodiments of the technologies presented herein offer certain advantages, including avoiding the use of an undesirable or burdensome physical keyboard or microphone; overcoming issues associated with time-consuming and/or high-latency processing of low-quality images of a user captured by a camera; allowing for capture and detection of subtle, small, or fast movements and/or variations in pressure on an object (e.g., varying amounts of force exerted through a stylus, writing instrument, or finger being pressed against a surface) that can be important for resolving, e.g., text input; collecting and analyzing various sensory information that enhances a control identification process, which may not be readily achievable using conventional input devices; and allowing for hand-based control to be possible in cases where a user's hand is obscured or outside a camera's field of view, e.g., in the user's pocket, or while the user is wearing a glove.

Some embodiments of the technology described herein are directed to coupling a system that senses neuromuscular signals, via neuromuscular sensors worn by a user, with a system that performs AR functions. In particular, a neuromuscular system that senses neuromuscular signals for the purpose of determining a position of a body part (e.g., a hand, an arm, etc.) may be used in conjunction with an AR system to provide an improved AR experience for a user. For instance, information gained within both systems may be used to improve the overall AR experience. The AR system may include a camera to capture image information regarding one or more body part(s) of the user, and this image information may be used to improve the user's interaction with an AR environment produced by the AR system. For example, a musculoskeletal representation associated with one or more body part(s) of the user may be generated based on sensor data from the neuromuscular sensors, and image data of the user, captured by the camera in the AR system, may be used to supplement the sensor data to, for instance, enable a more realistic visualization of the user relative to one or more object(s) in the AR environment. In one implementation of this example, the image data of the user may be used to determine an object of interest to the user, and the sensor data may provide muscle activation information used to determine a type of action to be performed relative to the object and/or an amount of force to be used for the action (e.g., a gentle push of the object, a forceful push of the object, a tap on the object, etc.). In another implementation, display information in the AR environment may be used as feedback to the user to permit the user to more accurately control his/her musculoskeletal input (e.g., movement input) to the neuromuscular system.

The inventors recognize that neither cameras nor neuromuscular sensors are by themselves ideal input systems. Cameras such as those that may be provided in an AR system may provide good positional information (relative both to other skeletal segments and to external objects) when, e.g., joint segments of the user are clearly within view, but may be limited by field of view restrictions and occlusion, and may be ill-suited for measuring forces. At the same time, signals measured or detected by neuromuscular sensors (e.g., electromyography (EMG) signals or another modality of neuromuscular signals as described herein) may, on their own, be insufficient for distinguishing between forces that a user is applying against himself/herself versus forces that he/she applies to an external object, and such signals may not provide sufficiently accurate information about skeletal geometry, for example finger lengths. According to some embodiments, it is appreciated that it would be beneficial to increase the accuracy of AR systems and neuromuscular-sensor-based systems to provide more accurate and more realistic user experiences.

Some conventional AR systems include camera-based technologies that are used to identify and map physical objects in the user's real-world environment. Such camera-based technologies are often insufficient in measuring and enabling a full range of possible physical and virtual interactions with physical objects in an AR environment generated by an AR system. To this end, some embodiments of the technology described herein are directed to an AR-based system comprising an improved AR system that provides an enriched AR user experience through interpretation of neuromuscular signals obtained via a wearable neuromuscular-sensor device worn by a user of the AR-based system. In some embodiments, motor activity states determined from the neuromuscular signals may be used to determine whether and how a user is interacting with a physical object in the AR environment. In other embodiments, the motor activity states determined from the neuromuscular signals may be used to change a mode of the AR system, e.g., to turn a physical object into one or more "augmented" object(s) by activating a set of control actions for the physical object in response to the determined motor activity states. In various embodiments, visual indicators based on the user's neuromuscular signals may be used to improve user experience when the user interacts with physical objects in the AR environment. Further examples of using neuromuscular signals to enhance interactions with physical objects in an AR environment are described in more detail below.

As will be appreciated, although various embodiments may be described herein with reference to an AR-based system, the scope of the present technology disclosed herein is such that those embodiments may be implemented using other types of XR-based systems.

In accordance with some embodiments of the technology disclosed herein, neuromuscular signals sensed and recorded by one or more wearable sensors may be used to determine information a user's interaction or desired interaction with a physical object in an AR environment generated by an AR-based system. Such signals may also be referred to as "sensed signals" herein. Sensed signals may be used directly as an input to an AR system (e.g. by using motor-unit action potentials as an input signal) and/or the sensed signals may be processed (including by using an inference model as described herein) for the purpose of determining a movement, a force, and/or a position of a part of the user's body (e.g. fingers, hand, wrist, etc.). For example, neuromuscular signals obtained by neuromuscular sensors arranged on a wearable device may be used to determine a force (e.g., a grasping force) applied to a physical object. The inventors have recognized that a number of muscular activation states of a user may be identified from the sensed signals and/or from information based on the sensed signals, to provide an improved AR experience. The muscular activation states may include, but are not limited to, a static gesture or pose performed by the user, a dynamic gesture or motion performed by the user, a sub-muscular activation state of the user, a muscular tensing or relaxation performed by the user, or any combination of the foregoing. As described herein, the user's interaction with one or more physical objects in the AR environment can take many forms, including but not limited to: selection of one or more objects, control of one or more objects, activation or deactivation of one or more objects, adjustment of settings or features relating to one or more objects, etc. As will be appreciated, the user's interaction may take other forms enabled by the AR system for the environment, and need not be the interactions specifically listed herein. For instance, control performed in an AR environment may include control based on activation of one or more individual motor units, e.g., control based on a detected sub-muscular activation state of the user, such as a sensed tensing of a muscle. As will be appreciated, the phrases "sensed", "obtained", "collected", "sensed and recorded", "measured", "recorded", and the like, when used in conjunction with a sensor signal from a neuromuscular sensor comprises a signal detected by the sensor. As will be appreciated, signal may be recorded, or sensed and recorded, without storage in a nonvolatile memory, or the signal may be recorded, or sensed and recorded, with storage in a local nonvolatile memory or in an external nonvolatile memory. For example, after detection, the signal may be stored at the sensor "as-detected" (i.e., raw), or the signal may undergo processing at the sensor prior to storage at the sensor, or the signal may be communicated (e.g., via a Bluetooth technology or the like) to an external device for processing and/or storage, or any combination of the foregoing.

Identification of one or more muscular activation state(s) may allow a layered or multi-level approach to interacting with physical objects in an AR environment. For instance, at a first layer/level, one muscular activation state may indicate that the user is interacting with a physical object; at a second layer/level, another muscular activation state may indicate that the user wants to activate a set of virtual controls and/or features for the physical object in the AR environment with which they are interacting; and at a third layer/level, yet another muscular activation state may indicate which of the activated virtual controls and/or features the user wants to use when interacting with the object. It will be appreciated that any number of muscular activation states and layers may be used without departing from the scope of this disclosure. For example, in some embodiments, one or more muscular activation state(s) may correspond to a concurrent gesture based on activation of one or more motor units, e.g., the user's hand bending at the wrist while pointing the index finger at the object. In some embodiments, one or more muscular activation state(s) may correspond to a sequence of gestures based on activation of one or more motor units, e.g., the user's hand grasping the object and lifting the object. In some embodiments, a single muscular activation state may both indicate a user's desire to interact with a physical object and to activate a set of virtual controls and/or features for interacting with the object.

As an example, sensor signals may be sensed and recorded for a first activity of the user, e.g., a first gesture performed by the user, and a first muscular activation state of the user may be identified from these sensed signals using, for example, a trained inference model, as discussed below. The first muscular activation state may indicate that the user is interacting with a particular physical object (e.g., a writing implement) in the user's environment. In response to the system detecting the first activity, feedback may be provided to identify the interaction with the physical object indicated by the first muscular activation state. Examples of the types of feedback that may be provided in accordance with some embodiments of the present technology are discussed in more detail below. Sensor signals may continue to be sensed and recorded, and a second muscular activation state may be determined. Responsive to identifying the second muscular activation state (e.g., corresponding to a second gesture, which may the same as or different from the first gesture), the AR system may activate a set of virtual controls (e.g., controls for selecting writing characteristics for a writing implement) for the object. Sensor signals may continue to be sensed and recorded, and a third muscular activation state may be determined. The third muscular activation state may indicate a selection from among the virtual controls. For example, the third muscular activation state may indicate a selection of a particular line thickness of the writing implement.

According to some embodiments, the muscular activation states may be identified, at least in part, from raw (e.g., unprocessed) sensor signals collected by one or more of the wearable sensors. In some embodiments, the muscular activation states may be identified, at least in part, from information based on the raw sensor signals (e.g., processed sensor signals), where the raw sensor signals collected by the one or more of the wearable sensors are processed to perform, e.g., amplification, filtering, rectification, and/or other form of signal processing, examples of which are described in more detail below. In some embodiments, the muscular activation states may be identified, at least in part, from an output of a trained inference model that receives the sensor signals (raw or processed versions of the sensor signals) as input.

As disclosed herein, muscular activation states, as determined based on sensor signals in accordance with one or more of the techniques described herein, may be used to interact with one or more physical object(s) in an AR environment without the need to rely on cumbersome and inefficient input devices, as discussed above. For example, sensor data (e.g., signals obtained from neuromuscular sensors or data derived from such signals) may be sensed and recorded, and muscular activation states may be identified from the sensor data without the user having to carry a controller and/or other input device(s), and without having the user remember complicated button or key manipulation sequences. Also, the identification of the muscular activation states (e.g., poses, gestures, etc.) from the sensor data can be performed relatively fast, thereby reducing the response times and latency associated with issuing control signals to the AR system. Furthermore, some embodiments of the technology described herein enable user customization of an AR-based system, such that each user may define a control scheme for interacting with physical objects in an AR environment of an AR system of the AR-based system, which is typically not possible with conventional AR systems.

Signals sensed by wearable sensors placed at locations on a user's body may be provided as input to an inference model trained to generate spatial information for rigid segments of a multi-segment articulated rigid-body model of a human body. The spatial information may include, for example, position information of one or more segments, orientation information of one or more segments, joint angles between segments, and the like. Based on the input, and as a result of training, the inference model may implicitly represent inferred motion of the articulated rigid body under defined movement constraints. The trained inference model may output data useable for applications such as applications for rendering a representation of the user's body in an XR environment (e.g., the AR environment mentioned above), in which the user may interact with one or more physical and/or one or more virtual object(s), and/or applications for monitoring the user's movements as the user performs a physical activity to assess, for example, whether the user is performing the physical activity in a desired manner. As will be appreciated, the output data from the trained inference model may be used for applications other than those specifically identified herein.

For instance, movement data obtained by a single movement sensor positioned on a user (e.g., on a user's wrist or arm) may be provided as input data to a trained inference model. Corresponding output data generated by the trained inference model may be used to determine spatial information for one or more segments of a multi-segment articulated rigid-body model for the user. For example, the output data may be used to determine the position and/or the orientation of one or more segments in the multi-segment articulated rigid body model. In another example, the output data may be used to determine angles between connected segments in the multi-segment articulated rigid-body model.

As will be appreciated, an inference model used in conjunction with neuromuscular signals may involve a generalized skeletal geometry for a type of user (e.g., a typical adult male, a typical child, a typical adult female) or may involve a user-specific skeletal geometry for a particular user.

Different types of sensors may be used to provide input data to a trained inference model, as discussed below.

As described briefly herein, in some embodiments of the present technology, various muscular activation states may be identified directly from sensor data. In other embodiments, handstates, gestures, postures, and the like (which may be referred to herein individually or collectively as muscular activation states) may be identified based, at least in part, on the output of a trained inference model. In some embodiments, the trained inference model may output motor-unit or muscle activations and/or position, orientation, and/or force estimates for segments of a computer-generated musculoskeletal model. In one example, all or portions of the human musculoskeletal system can be modeled as a multi-segment articulated rigid body system, with joints forming the interfaces between the different segments, and with joint angles defining the spatial relationships between connected segments in the model.

As used herein, the term "gestures" may refer to a static or dynamic configuration of one or more body parts including a position of the one or more body parts and forces associated with the configuration. For example, gestures may include discrete gestures, such as placing or pressing the palm of a hand down on a solid surface or grasping a ball, continuous gestures, such as waving a finger back and forth, grasping and throwing a ball, or a combination of discrete and continuous gestures. Gestures may include covert gestures that may be imperceptible to another person, such as slightly tensing a joint by co-contracting opposing muscles or using sub-muscular activations. In training an inference model, gestures may be defined using an application configured to prompt a user to perform the gestures or, alternatively, gestures may be arbitrarily defined by a user. The gestures performed by the user may include symbolic gestures (e.g., gestures mapped to other gestures, interactions, or commands, for example, based on a gesture vocabulary that specifies the mapping). In some cases, hand and arm gestures may be symbolic and used to communicate according to cultural standards.

In some embodiments of the technology described herein, sensor signals may be used to predict information about a position and/or a movement of a portion of a user's arm and/or the user's hand, which may be represented as a multi-segment articulated rigid-body system with joints connecting the multiple segments of the rigid-body system. For example, in the case of a hand movement, signals sensed and recorded by wearable neuromuscular sensors placed at locations on the user's body (e.g., the user's arm and/or wrist) may be provided as input to an inference model trained to predict estimates of the position (e.g., absolute position, relative position, orientation) and the force(s) associated with a plurality of rigid segments in a computer-based musculoskeletal representation associated with a hand when the user performs one or more hand movements. The combination of position information and force information associated with segments of a musculoskeletal representation associated with a hand may be referred to herein as a "handstate" of the musculoskeletal representation. As a user performs different movements, a trained inference model may interpret neuromuscular signals sensed and recorded by the wearable neuromuscular sensors into position and force estimates (handstate information) that are used to update the musculoskeletal representation. Because the neuromuscular signals may be continuously sensed and recorded, the musculoskeletal representation may be updated in real time and a visual representation of a hand (e.g., within an AR environment) may be rendered based on current estimates of the handstate. As will be appreciated, an estimate of a user's handstate may be used to determine a gesture being performed by the user and/or to predict a gesture that the user will perform.

Constraints on the movement at a joint are governed by the type of joint connecting the segments and the biological structures (e.g., muscles, tendons, ligaments) that may restrict the range of movement at the joint. For example, a shoulder joint connecting the upper arm to a torso of a human subject, and a hip joint connecting an upper leg to the torso, are ball and socket joints that permit extension and flexion movements as well as rotational movements. By contrast, an elbow joint connecting the upper arm and a lower arm (or forearm), and a knee joint connecting the upper leg and a lower leg of the human subject, allow for a more limited range of motion. In this example, a multi-segment articulated rigid body system may be used to model portions of the human musculoskeletal system. However, it should be appreciated that although some segments of the human musculoskeletal system (e.g., the forearm) may be approximated as a rigid body in the articulated rigid body system, such segments may each include multiple rigid structures (e.g., the forearm may include ulna and radius bones), which may enable more complex movements within the segment that is not explicitly considered by the rigid body model. Accordingly, a model of an articulated rigid body system for use with some embodiments of the technology described herein may include segments that represent a combination of body parts that are not strictly rigid bodies. It will be appreciated that physical models other than the multi-segment articulated rigid body system may be used to model portions of the human musculoskeletal system without departing from the scope of this disclosure.

Continuing with the example above, in kinematics, rigid bodies are objects that exhibit various attributes of motion (e.g., position, orientation, angular velocity, acceleration). Knowing the motion attributes of one segment of a rigid body enables the motion attributes for other segments of the rigid body to be determined based on constraints in how the segments are connected. For example, the hand may be modeled as a multi-segment articulated body, with joints in the wrist and each finger forming interfaces between the multiple segments in the model. In some embodiments, movements of the segments in the rigid body model can be simulated as an articulated rigid body system in which position (e.g., actual position, relative position, or orientation) information of a segment relative to other segments in the model are predicted using a trained inference model.

For some embodiments of the present technology described herein, the portion of the human body approximated by a musculoskeletal representation is a hand or a combination of a hand with one or more arm segments. The information used to describe a current state of the positional relationships between segments, force relationships for individual segments or combinations of segments, and muscle and motor unit activation relationships between segments, in the musculoskeletal representation is referred to herein as the handstate of the musculoskeletal representation (see discussion above). It should be appreciated, however, that the techniques described herein are also applicable to musculoskeletal representations of portions of the body other than the hand including, but not limited to, an arm, a leg, a foot, a torso, a neck, or any combination of the foregoing.

In addition to spatial (e.g., position and/or orientation) information, some embodiments enable a prediction of force information associated with one or more segments of the musculoskeletal representation. For example, linear forces or rotational (torque) forces exerted by one or more segments may be estimated. Examples of linear forces include, but are not limited to, the force of a finger or hand pressing on a solid object such as a table, and a force exerted when two segments (e.g., two fingers) are pinched together. Examples of rotational forces include, but are not limited to, rotational forces created when a segment, such as in a wrist or a finger, is twisted or flexed relative to another segment. In some embodiments, the force information determined as a portion of a current handstate estimate includes one or more of pinching force information, grasping force information, and information about co-contraction forces between muscles represented by the musculoskeletal representation.

Turning now to the figures, FIG. 1 schematically illustrates a system 100, for example, a neuromuscular activity system, in accordance with some embodiments of the technology described herein. The system 100 may comprise one or more sensor(s) 110 configured to sense and record signals resulting from activation of motor units within one or more portion(s) of a human body. The sensor(s) 110 may include one or more neuromuscular sensor(s) configured to sense and record signals arising from neuromuscular activity in skeletal muscle of a human body. The term "neuromuscular activity" as used herein refers to neural activation of spinal motor neurons or units that innervate a muscle, muscle activation, muscle contraction, or any combination of the neural activation, muscle activation, and muscle contraction. The one or more neuromuscular sensor(s) may include one or more electromyography (EMG) sensors, one or more mechanomyography (MMG) sensors, one or more sonomyography (SMG) sensors, a combination of two or more types of EMG sensors, MMG sensors, and SMG sensors, and/or one or more sensors of any suitable type able to detect neuromuscular signals. In some embodiments, information relating to an interaction of a user with a physical object in an AR environment may be determined from neuromuscular signals sensed by the one or more neuromuscular sensor(s). Spatial information (e.g., position and/or orientation information) and force information relating to the movement may be predicted based on the sensed neuromuscular signals as the user moves over time. In some embodiments, the one or more neuromuscular sensor(s) may sense muscular activity related to movement caused by external objects, for example, movement of a hand being pushed by an external object.

The one or more sensor(s) 110 may include one or more auxiliary sensor(s), such as one or more Inertial Measurement Unit(s) or IMU(s), which measure a combination of physical aspects of motion, using, for example, an accelerometer, a gyroscope, a magnetometer, or any combination of one or more accelerometers, gyroscopes and magnetometers. In some embodiments, one or more IMU(s) may be used to sense information about movement of the part of the body on which the IMU(s) is or are attached, and information derived from the sensed IMU data (e.g., position and/or orientation information) may be tracked as the user moves over time. For example, one or more IMU(s) may be used to track movements of portions (e.g., arms, legs) of a user's body proximal to the user's torso relative to the IMU(s) as the user moves over time.

In embodiments that include at least one IMU and one or more neuromuscular sensor(s), the IMU(s) and the neuromuscular sensor(s) may be arranged to detect movement of different parts of a human body. For example, the IMU(s) may be arranged to detect movements of one or more body segments proximal to the torso (e.g., movements of an upper arm), whereas the neuromuscular sensors may be arranged to detect motor unit activity within one or more body segments distal to the torso (e.g., movements of a lower arm (forearm) or a wrist). It should be appreciated, however, that the sensors (i.e., the IMU(s) and the neuromuscular sensor(s)) may be arranged in any suitable way, and embodiments of the technology described herein are not limited based on the particular sensor arrangement. For example, in some embodiments, at least one IMU and a plurality of neuromuscular sensors may be co-located on a body segment to track motor unit activity and/or movements of the body segment using different types of measurements. In one implementation, an IMU and a plurality of EMG sensors may be arranged on a wearable device structured to be worn around the lower arm or the wrist of a user. In such an arrangement, the IMU may be configured to track, over time, movement information (e.g., positioning and/or orientation) associated with one or more arm segments, to determine, for example, whether the user has raised or lowered his/her arm, whereas the EMG sensors may be configured to determine finer-grained or more subtle movement information and/or sub-muscular information associated with activation of muscular or sub-muscular structures in muscles of the wrist and/or the hand.

As the tension of a muscle increases during performance of a motor task, the firing rates of active neurons increases and additional neurons may become active, which is a process that may be referred to as motor-unit recruitment. The pattern by which neurons become active and increase their firing rate is stereotyped, such that expected motor-unit recruitment patterns, may define an activity manifold associated with standard or normal movement. In some embodiments, sensor signals may identify activation of a single motor unit or a group of motor units that are "off-manifold," in that the pattern of motor-unit activation is different than an expected or typical motor-unit recruitment pattern. Such off-manifold activation may be referred to herein as "sub-muscular activation" or "activation of a sub-muscular structure," where a sub-muscular structure refers to the single motor unit or the group of motor units associated with the off-manifold activation. Examples of off-manifold motor-unit recruitment patterns include, but are not limited to, selectively activating a higher-threshold motor unit without activating a lower-threshold motor unit that would normally be activated earlier in the recruitment order and modulating the firing rate of a motor unit across a substantial range without modulating the activity of other neurons that would normally be co-modulated in typical motor-unit recruitment patterns. In some embodiments, the one or more neuromuscular sensors may be arranged relative to the human body and used to sense sub-muscular activation without observable movement, i.e., without a corresponding movement of the body that can be readily observed. Sub-muscular activation may be used, at least in part, to interact with physical objects in an AR environment, in accordance with some embodiments of the technology described herein.

Some or all of the sensor(s) 110 may each include one or more sensing components configured to sense information about a user. In the case of IMUs, the sensing component(s) of an IMU may include one or more: accelerometer, gyroscope, magnetometer, or any combination thereof, to measure or sense characteristics of body motion, examples of which include, but are not limited to, acceleration, angular velocity, and a magnetic field around the body during the body motion. In the case of neuromuscular sensors, the sensing component(s) may include, but are not limited to, electrodes that detect electric potentials on the surface of the body (e.g., for EMG sensors), vibration sensors that measure skin surface vibrations (e.g., for MMG sensors), acoustic sensing components that measure ultrasound signals (e.g., for SMG sensors) arising from muscle activity, or any combination thereof. Optionally, the sensor(s) 110 may include any one or any combination of: a thermal sensor that measures the user's skin temperature (e.g., a thermistor); a cardio sensor that measure's the user's pulse, heart rate, a moisture sensor that measures the user's state of perspiration, and the like. Exemplary sensors that may be used as part of the one or more sensor(s) 110, in accordance with some embodiments of the technology disclosed herein, are described in more detail in U.S. Pat. No. 10,409,371 entitled "METHODS AND APPARATUS FOR INFERRING USER INTENT BASED ON NEUROMUSCULAR SIGNALS," which is incorporated by reference herein.

Figure 6B:
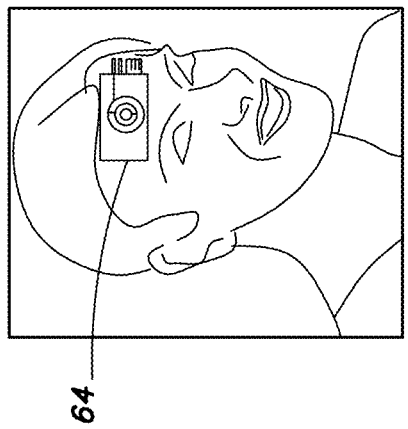
FIGS. 6A, 6B, 6C, and 6D schematically illustrate patch type wearable systems with sensor electronics incorporated thereon, in accordance with some embodiments of the technology described herein.
Figure 6D:
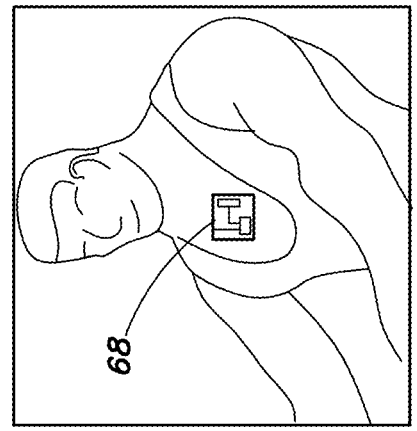
Figure 6A:
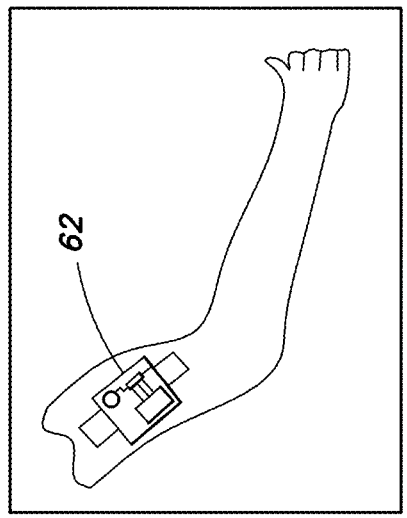
Figure 6C:
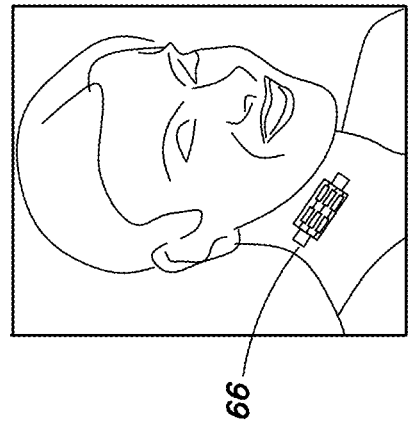

In some embodiments, the one or more sensor(s) 110 may comprise a plurality of sensors 110, and at least some of the plurality of sensors 110 may be arranged as a portion of a wearable device structured to be worn on or around a part of a user's body. For example, in one non-limiting example, an IMU and a plurality of neuromuscular sensors may be arranged circumferentially on an adjustable and/or elastic band, such as a wristband or an armband structured to be worn around a user's wrist or arm, as described in more detail below. In some embodiments, multiple wearable devices, each having one or more IMU(s) and/or one or more neuromuscular sensor(s) included thereon, may be used to determine information relating to an interaction of a user with a physical object based on activation from sub-muscular structures and/or based on movement that involve multiple parts of the body. Alternatively, at least some of the sensors 110 may be arranged on a wearable patch structured to be affixed to a portion of the user's body. FIGS. 6A-6D show various types of wearable patches. FIG. 6A shows a wearable patch 62 in which circuitry for an electronic sensor may be printed on a flexible substrate that is structured to adhere to an arm, e.g., near a vein to sense blood flow in the user. The wearable patch 62 may be an RFID-type patch, which may transmit sensed information wirelessly upon interrogation by an external device. FIG. 6B shows a wearable patch 64 in which an electronic sensor may be incorporated on a substrate that is structured to be worn on the user's forehead, e.g., to measure moisture from perspiration. The wearable patch 64 may include circuitry for wireless communication, or may include a connector structured to be connectable to a cable, e.g., a cable attached to a helmet, a heads-mounted display, or another external device. The wearable patch 64 may be structured to adhere to the user's forehead or to be held against the user's forehead by, e.g., a headband, skullcap, or the like. FIG. 6C shows a wearable patch 66 in which circuitry for an electronic sensor may be printed on a substrate that is structured to adhere to the user's neck, e.g., near the user's carotid artery to sense flood flow to the user's brain. The wearable patch 66 may be an RFID-type patch or may include a connector structured to connect to external electronics. FIG. 6D shows a wearable patch 68 in which an electronic sensor may be incorporated on a substrate that is structured to be worn near the user's heart, e.g., to measure the user's heartrate or to measure blood flow to/from the user's heart. As will be appreciated, wireless communication is not limited to RFID technology, and other communication technologies may be employed. Also, as will be appreciated, the sensors 110 may be incorporated on other types of wearable patches that may be structured differently from those shown in FIGS. 6A-6D.

Figure 7A:
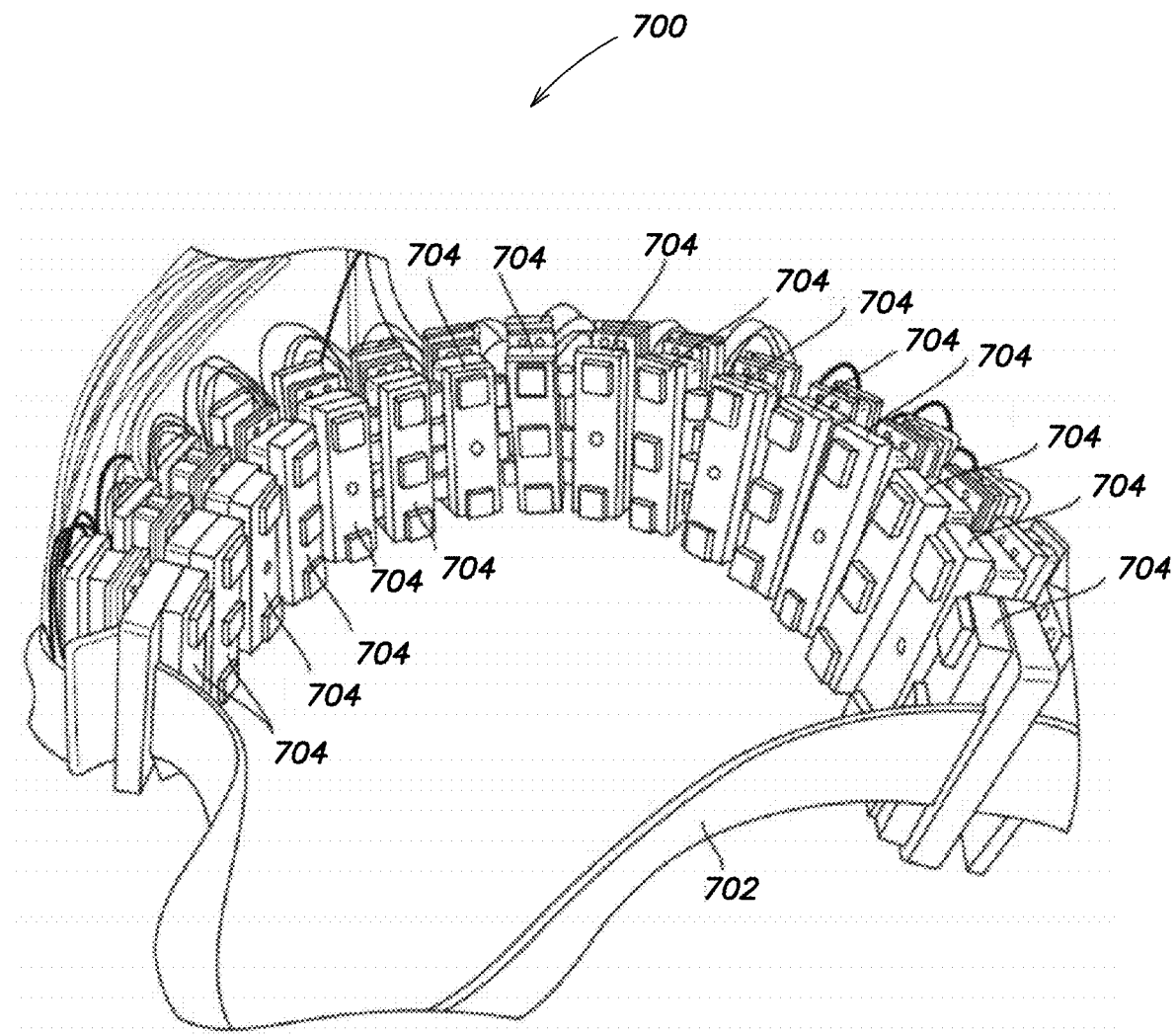
FIG. 7A illustrates a wristband having EMG sensors arranged circumferentially thereon, in accordance with some embodiments of the technology described herein.

In one implementation, the sensor(s) 110 may include sixteen neuromuscular sensors arranged circumferentially around a band (e.g., an elastic band) structured to be worn around a user's lower arm (e.g., encircling the user's forearm). For example, FIG. 7A shows an embodiment of a wearable system in which neuromuscular sensors 704 (e.g., EMG sensors) are arranged circumferentially around an elastic band 702. It should be appreciated that any suitable number of neuromuscular sensors may be used and the number and arrangement of neuromuscular sensors used may depend on the particular application for which the wearable system is used. For example, a wearable armband or wristband may be used to generate control information for controlling a robot, controlling a vehicle, scrolling through text, controlling a virtual avatar, or any other suitable control task. In some embodiments, the elastic band 702 may also include one or more IMUs (not shown).

Figure 7B:
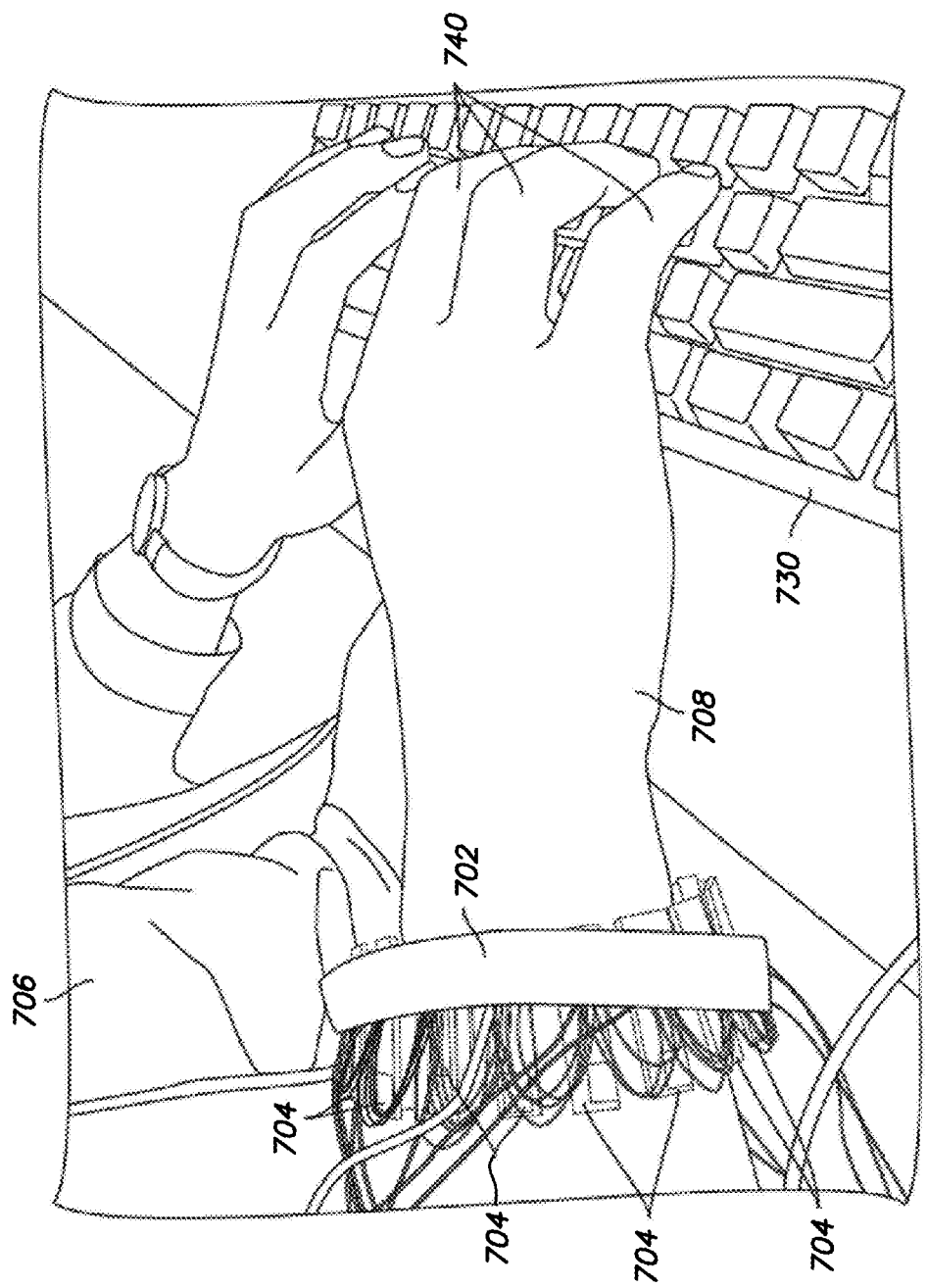
FIG. 7B illustrates a user wearing the wristband of FIG. 7A, while performing a typing task.

For example, as shown in FIG. 7B, a user 706 may wear the elastic band 702 on his/her hand 708. In this way, the neuromuscular sensors 704 (e.g., EMG sensors) may be configured to sense and record neuromuscular signals as the user 706 controls or manipulates a keyboard 730 using his/her fingers 740. In some embodiments, the elastic band 702 may also include one or more IMUs (not shown), configured to sense and obtain or record movement information, as discussed above.

Figure 8A:
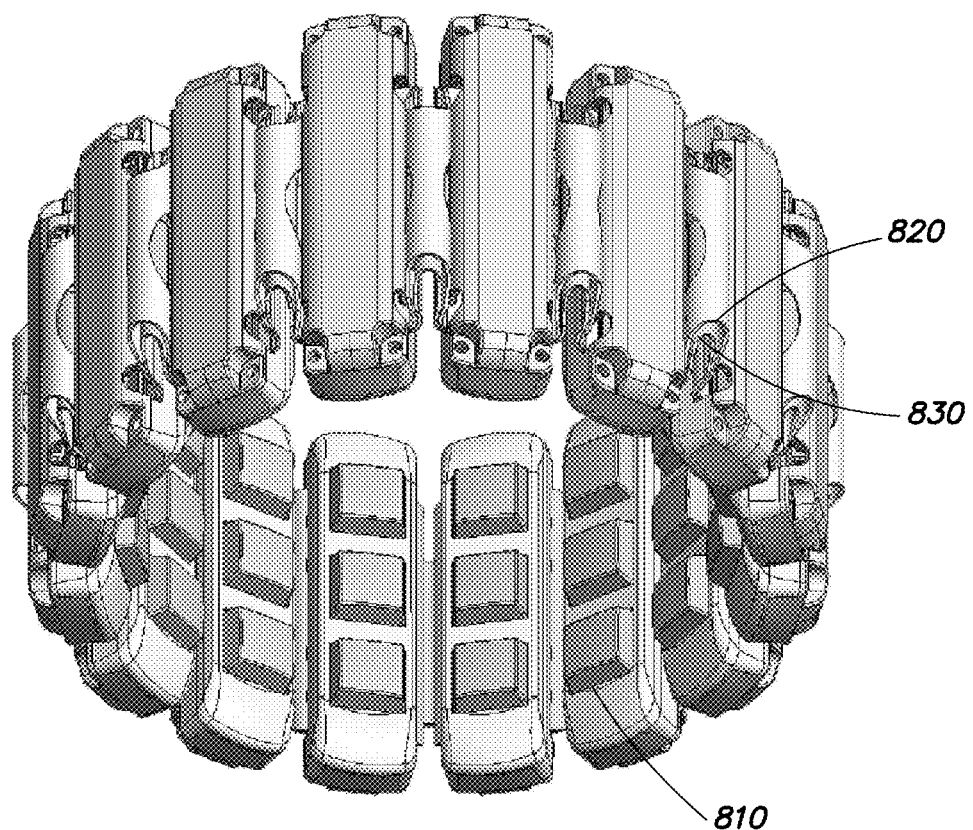
FIG. 8A illustrates a wearable system with sixteen EMG sensors arranged circumferentially around a band configured to be worn around a user's lower arm or wrist, in accordance with some embodiments of the technology described herein.

FIGS. 8A-8B and 9A-9B show other embodiments of a wearable system of the present technology. In particular, FIG. 8A illustrates a wearable system with a plurality of sensors 810 arranged circumferentially around an elastic band 820 structured to be worn around a user's lower arm or wrist. The sensors 810 may be neuromuscular sensors (e.g., EMG sensors). As shown, there may be sixteen sensors 810 arranged circumferentially around the elastic band 820 at a regular spacing. It should be appreciated that any suitable number of sensors 810 may be used, and the spacing need not be regular. The number and arrangement of the sensors 810 may depend on the particular application for which the wearable system is used. For instance, the number and arrangement of the sensors 810 may differ when the wearable system is to be worn on a wrist in comparison with a thigh. A wearable system (e.g., armband, wristband, thigh-band, etc.) can be used to generate control information for controlling a robot, controlling a vehicle, scrolling through text, controlling a virtual avatar, and/or performing any other suitable control task.

Figure 8B:
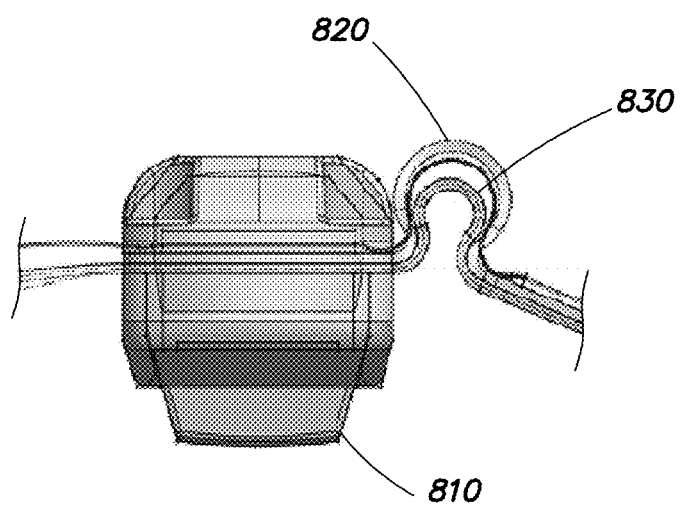
FIG. 8B is a cross-sectional view through one of the sixteen EMG sensors illustrated in FIG. 8A.

In some embodiments, the sensors 810 may include only a set of neuromuscular sensors (e.g., EMG sensors). In other embodiments, the sensors 810 may include a set of neuromuscular sensors and at least one auxiliary device. The auxiliary device(s) may be configured to continuously sense and record one or a plurality of auxiliary signal(s). Examples of auxiliary devices include, but are not limited to, IMUs, microphones, imaging devices (e.g., cameras), radiation-based sensors for use with a radiation-generation device (e.g., a laser-scanning device), heart-rate monitors, and other types of devices, which may capture a user's condition or other characteristics of the user. As shown in FIG. 8A, the sensors 810 may be coupled together using flexible electronics 830 incorporated into the wearable system. FIG. 8B illustrates a cross-sectional view through one of the sensors 810 of the wearable system shown in FIG. 8A.

In some embodiments, the output(s) of one or more of sensing component(s) of the sensors 810 can be optionally processed using hardware signal-processing circuitry (e.g., to perform amplification, filtering, and/or rectification). In other embodiments, at least some signal processing of the output(s) of the sensing component(s) can be performed using software. Thus, signal processing of signals sampled by the sensors 810 can be performed by hardware or by software, or by any suitable combination of hardware and software, as aspects of the technology described herein are not limited in this respect. A non-limiting example of a signal-processing procedure used to process recorded data from the sensors 810 is discussed in more detail below in connection with FIGS. 9A and 9B.

FIGS. 9A and 9B illustrate a schematic diagram with internal components of a wearable system with sixteen sensors (e.g., EMG sensors), in accordance with some embodiments of the technology described herein. As shown, the wearable system includes a wearable portion 910 (FIG. 9A) and a dongle portion 920 (FIG. 9B). Although not illustrated, the dongle portion 920 is in communication with the wearable portion 910 (e.g., via Bluetooth or another suitable short range wireless communication technology). As shown in FIG. 9A, the wearable portion 910 includes the sensors 810, examples of which are described above in connection with FIGS. 8A and 8B. The sensors 810 provide output (e.g., signals) to an analog front end 930, which performs analog processing (e.g., noise reduction, filtering, etc.) on the signals. Processed analog signals produced by the analog front end 930 are then provided to an analog-to-digital converter 932, which converts the processed analog signals to digital signals that can be processed by one or more computer processors. An example of a computer processor that may be used in accordance with some embodiments is a microcontroller (MCU) 934. As shown in FIG. 9A, the MCU 934 may also receive inputs from other sensors (e.g., an IMU 940) and from a power and battery module 942. As will be appreciated, the MCU 934 may receive data from other devices not specifically shown. A processing output by the MCU 934 may be provided to an antenna 950 for transmission to the dongle portion 920, shown in FIG. 9B.

The dongle portion 920 includes an antenna 952 that communicates with the antenna 950 of the wearable portion 910. Communication between the antennas 950 and 952 may occur using any suitable wireless technology and protocol, non-limiting examples of which include radiofrequency signaling and Bluetooth. As shown, the signals received by the antenna 952 of the dongle portion 920 may be provided to a host computer for further processing, for display, and/or for effecting control of a particular physical or virtual object or objects (e.g., to perform a control operation in an AR environment).

Although the examples provided with reference to FIGS. 8A, 8B, 9A, and 9B are discussed in the context of interfaces with EMG sensors, it is to be understood that the wearable systems described herein can also be implemented with other types of sensors, including, but not limited to, mechanomyography (MMG) sensors, sonomyography (SMG) sensors, and electrical impedance tomography (EIT) sensors.

Returning to FIG. 1, in some embodiments, sensor data or signals obtained by the sensor(s) 110 may be optionally processed to compute additional derived measurements, which may then be provided as input to an inference model, as described in more detail below. For example, signals obtained from an IMU may be processed to derive an orientation signal that specifies the orientation of a segment of a rigid body over time. The sensor(s) 110 may implement signal processing using components integrated with the sensing components of the sensor(s) 110, or at least a portion of the signal processing may be performed by one or more components in communication with, but not directly integrated with, the sensing components of the sensor(s) 110.

The system 100 also includes one or more computer processor(s) 112 programmed to communicate with the sensor(s) 110. For example, signals obtained by one or more of the sensor(s) 110 may be output from the sensor(s) 110 and provided to the processor(s) 112, which may be programmed to execute one or more machine-learning algorithm(s) to process the signals output by the sensor(s) 110. The algorithm(s) may process the signals to train (or retrain) one or more inference model(s) 114, and the trained (or retrained) inference model(s) 114 may be stored for later use in generating selection signals and/or control signals for controlling an AR system, as described in more detail below. As will be appreciated, in some embodiments, the inference model(s) 114 may include at least one statistical model.

In some embodiments, the inference model(s) 114 may include a neural network and, for example, may be a recurrent neural network. In some embodiments, the recurrent neural network may be a long short-term memory (LSTM) neural network. It should be appreciated, however, that the recurrent neural network is not limited to being an LSTM neural network and may have any other suitable architecture. For example, in some embodiments, the recurrent neural network may be any one or any combination of: a fully recurrent neural network, a gated recurrent neural network, a recursive neural network, a Hopfield neural network, an associative memory neural network, an Elman neural network, a Jordan neural network, an echo state neural network, and a second-order recurrent neural network, and/or any other suitable type of recurrent neural network. In other embodiments, neural networks that are not recurrent neural networks may be used. For example, deep neural networks, convolutional neural networks, and/or feedforward neural networks may be used.

In some embodiments, the inference model(s) 114 may produce discrete outputs. Discrete outputs (e.g., discrete classifications) may be used, for example, when a desired output is to know whether a particular pattern of activation (including individual neural spiking events) is detected in the neuromuscular signals. For example, the inference model(s) 114 may be trained to estimate whether the user is activating a particular motor unit, activating a particular motor unit with a particular timing, activating a particular motor unit with a particular firing pattern, or activating a particular combination of motor units. On a shorter timescale, a discrete classification may be used in some embodiments to estimate whether a particular motor unit fired an action potential within a given amount of time. In such a scenario, these estimates may then be accumulated to obtain an estimated firing rate for that motor unit.

In embodiments in which an inference model is implemented as a neural network configured to output a discrete output (e.g., a discrete signal), the neural network may include an output layer that is a softmax layer, such that outputs of the inference model add up to one and may be interpreted as probabilities. For instance, outputs of the softmax layer may be a set of values corresponding to a respective set of control signals, with each value indicating a probability that the user wants to perform a particular control action. As one non-limiting example, the outputs of the softmax layer may be a set of three probabilities (e.g., 0.92, 0.05, and 0.03) indicating the respective probabilities that a detected pattern of activity is one of three known patterns.

It should be appreciated that when an inference model is a neural network configured to output a discrete output (e.g., a discrete signal), the neural network is not required to produce outputs that add up to one. For example, instead of a softmax layer, the output layer of the neural network may be a sigmoid layer, which does not restrict the outputs to probabilities that add up to one. In such embodiments, the neural network may be trained with a sigmoid cross-entropy cost. Such an implementation may be advantageous in cases where multiple different control actions may occur within a threshold amount of time and it is not important to distinguish an order in which these control actions occur (e.g., a user may activate two patterns of neural activity within the threshold amount of time). In some embodiments, any other suitable non-probabilistic multi-class classifier may be used, as aspects of the technology described herein are not limited in this respect.

In some embodiments, an output of the inference model(s) 114 may be a continuous signal rather than a discrete output (e.g., a discrete signal). For example, the model(s) 114 may output an estimate of a firing rate of each motor unit, or the model(s) 114 may output a time-series electrical signal corresponding to each motor unit or submuscular structure.

It should be appreciated that aspects of the technology described herein are not limited to using neural networks, as other types of inference models may be employed in some embodiments. For example, in some embodiments, the inference model(s) 114 may comprise a hidden Markov model (HMM), a switching HMM in which switching allows for toggling among different dynamic systems, dynamic Bayesian networks, and/or any other suitable graphical model having a temporal component. Any such inference model may be trained using sensor signals obtained by the sensor(s) 110.

As another example, in some embodiments, the inference model(s) 114 may be or may include a classifier that takes, as input, features derived from the sensor signals obtained by the sensor(s) 110. In such embodiments, the classifier may be trained using features extracted from the sensor signals. The classifier may be, e.g., a support vector machine, a Gaussian mixture model, a regression based classifier, a decision tree classifier, a Bayesian classifier, and/or any other suitable classifier, as aspects of the technology described herein are not limited in this respect. Input features to be provided to the classifier may be derived from the sensor signals in any suitable way. For example, the sensor signals may be analyzed as timeseries data using wavelet analysis techniques (e.g., continuous wavelet transform, discrete-time wavelet transform, etc.), Fourier-analytic techniques (e.g., short-time Fourier transform, Fourier transform, etc.), and/or any other suitable type of time-frequency analysis technique. As one non-limiting example, the sensor signals may be transformed using a wavelet transform and the resulting wavelet coefficients may be provided as inputs to the classifier.

In some embodiments, values for parameters of the inference model(s) 114 may be estimated from training data. For example, when the inference model(s) 114 is or includes a neural network, parameters of the neural network (e.g., weights) may be estimated from the training data. In some embodiments, parameters of the inference model(s) 114 may be estimated using gradient descent, stochastic gradient descent, and/or any other suitable iterative optimization technique. In embodiments where the inference model(s) 114 is or includes a recurrent neural network (e.g., an LSTM), the inference model(s) 114 may be trained using stochastic gradient descent and backpropagation through time. The training may employ a cross-entropy loss function and/or any other suitable loss function, as aspects of the technology described herein are not limited in this respect.

The system 100 also may include one or more controller(s) 116. For example, the controller(s) 116 may include a display controller configured to display a visual representation (e.g., a representation of a hand) on a display device (e.g., a display monitor). As discussed in more detail below, one or more computer processor(s) 112 may implement one or more trained inference models that receive, as input, sensor signals obtained by the sensor(s) 110 and that provide, as output, information (e.g., predicted handstate information) that is used to generate control signals that may be used to control, for example, an AR system.

The system 100 also may optionally include a user interface 118. Feedback determined based on the signals obtained by the sensor(s) 110 and processed by the processor(s) 112 may be provided via the user interface 118 to facilitate a user's understanding of how the system 100 is interpreting the user's muscular activity (e.g., an intended muscle movement). The user interface 118 may be implemented in any suitable way, including, but not limited to, an audio interface, a video interface, a tactile interface, and electrical stimulation interface, or any combination of the foregoing.

The system 100 may have an architecture that may take any suitable form. Some embodiments may employ a thin architecture in which the processor(s) 112 is or are included as a portion of a device separate from and in communication with the sensor(s) 110 arranged on the one or more wearable device(s). The sensor(s) 110 may be configured to wirelessly stream, in substantially real time, sensor signals and/or information derived from the sensor signals to the processor(s) 112 for processing. The device separate from and in communication with the sensors(s) 110 may be, for example, any one or any combination of: a remote server, a desktop computer, a laptop computer, a smartphone, a wearable electronic device such as a smartwatch, a health monitoring device, smart glasses, and an AR system.

Some embodiments employ a thick architecture in which the processor(s) 112 may be integrated with the one or more wearable device(s) on which the sensor(s) 110 is or are arranged. In yet further embodiments, processing of signals obtained by the sensor(s) 110 may be divided between multiple processors, at least one of which may be integrated with the sensor(s) 110, and at least one of which may be included as a portion of a device separate from and in communication with the sensor(s) 110. In such an implementation, the sensor(s) 110 may be configured to transmit at least some of the sensed signals to a first computer processor remotely located from the sensor(s) 110. The first computer processor may be programmed to train, based on the transmitted signals obtained by the sensor(s) 110, at least one inference model of the at least one inference model(s) 114. The first computer processor may then be programmed to transmit the trained at least one inference model to a second computer processor integrated with the one or more wearable devices on which the sensor(s) 110 is or are arranged. The second computer processor may be programmed to determine information relating to an interaction between a user wearing the one or more wearable device(s) and a physical object in an AR environment using the trained at least one inference model transmitted from the first computer processor. In this way, the training/fitting process and a real-time process that utilizes the trained at least one model may be performed separately by using different processors.

In some embodiments, a computer application that simulates and XR environment, (e.g., a VR environment, an AR environment, etc.) may be instructed to provide a visual representation by displaying a visual character, such as an avatar (e.g., via the controller(s) 116). Positioning, movement, and/or forces applied by portions of visual character within the XR environment may be displayed based on an output of the trained inference model(s). The visual representation may be dynamically updated as continuous signals are obtained by the sensor(s) 110 and processed by the trained inference model(s) 114 to provide a computer-generated representation of the character's movement that is updated in real-time.

Information obtained by or provided to the system 100, (e.g., inputs obtained from an AR camera, inputs obtained from the sensor(s) 110) can be used to improve user experience, accuracy, feedback, inference models, calibration functions, and other aspects in the overall system. To this end, in an AR environment for example, the system 100 may include an AR system that includes one or more processors, a camera, and a display (e.g., the user interface 118, or other interface via AR glasses or another viewing device) that provides AR information within a view of a user. The system 100 may also include system elements that couple the AR system with a computer-based system that generates a musculoskeletal representation based on sensor data (e.g., signals from at least one neuromuscular sensor). For example, the systems may be coupled via a special-purpose or other type of computer system that receives inputs from the AR system that generates a computer-based musculoskeletal representation. Such a system may include a gaming system, robotic control system, personal computer, or other system that is capable of interpreting AR and musculoskeletal information. The AR system and the system that generates the computer-based musculoskeletal representation may also be programmed to communicate directly. Such information may be communicated using any number of interfaces, protocols, and/or media.

As discussed above, some embodiments are directed to using an inference model 114 for predicting musculoskeletal information based on signals obtained by wearable sensors. As discussed briefly above in the example where portions of the human musculoskeletal system can be modeled as a multi-segment articulated rigid body system, the types of joints between segments in a multi-segment articulated rigid body model may serve as constraints that constrain movement of the rigid body. Additionally, different human individuals may move in characteristic ways when performing a task that can be captured in statistical patterns that may be generally applicable to individual user behavior. At least some of these constraints on human body movement may be explicitly incorporated into one or more inference model(s) (e.g., the model(s) 114) used for prediction of user movement, in accordance with some embodiments. Additionally or alternatively, the constraints may be learned by the inference model(s) 114 though training based on sensor data obtained from the sensor(s) 110, as discussed briefly above.

Some embodiments are directed to using an inference model for predicting information to generate a computer-based musculoskeletal representation and/or to update in real-time a computer-based musculoskeletal representation. For example, the predicted information may be predicted handstate information. The inference model may be used to predict the information based on IMU signals, neuromuscular signals (e.g., EMG, MMG, and/or SMG signals), external or auxiliary device signals (e.g., camera or laser-scanning signals), or a combination of IMU signals, neuromuscular signals, and external or auxiliary device signals detected as a user performs one or more movements. For instance, as discussed above, a camera associated with an AR system may be used to capture data of an actual position of a human subject of the computer-based musculoskeletal representation, and such actual-position information may be used to improve the accuracy of the representation. Further, outputs of the inference model may be used to generate a visual representation of the computer-based musculoskeletal representation in an AR environment. For example, a visual representation of muscle groups firing, force being applied, text being entered via movement, or other information produced by the computer-based musculoskeletal representation may be rendered in a visual display of an AR system. In some embodiments, other input/output devices (e.g., auditory inputs/outputs, haptic devices, etc.) may be used to further improve the accuracy of the overall system and/or to improve user experience.

Some embodiments of the technology described herein are directed to using an inference model, at least in part, to map muscular activation state information, which is information identified from neuromuscular signals obtained by neuromuscular sensors, to control signals. The inference model may receive as input IMU signals, neuromuscular signals (e.g., EMG, MMG, and SMG signals), external device signals (e.g., camera or laser-scanning signals), or a combination of IMU signals, neuromuscular signals, and external or auxiliary device signals detected as a user performs one or more sub-muscular activations, one or more movements, and/or one or more gestures. The inference model may be used to predict control information without the user having to make perceptible movements.

As discussed above, according to some embodiments of the present technology, camera information may be used to improve interpretation of neuromuscular signals and their relationship to movement, position, and force generation. As will be appreciated, the camera information may be, for example, an image signal corresponding to at least one image captured by a camera; thus, as used herein, an image from a camera may be understood to refer to an image signal from a camera. The camera may be a still camera, a video camera, an infrared camera, and the like, which is able to capture or record an image of a user. One or more filters may be used on the camera, so that the camera may capture images only within a particular range of wavelengths of light. As will be appreciated, the image may be a still image, a sequence of still images (or image sequence), a moving image (or video sequence), and the like, which may be captured and recorded as a signal. The terms "camera information," "camera data," and "camera signal," may be used herein to represent information about the user that may be captured by a camera. It should be understood that although various embodiments may refer to "a" camera or "the" camera, such embodiments may utilize two or more cameras instead of one camera. Further, the camera information may relate to any one or any combination of: an image produced by visible light, an image produced by non-visible (e.g., infrared) light, an image produced by light of a predetermined range of wavelengths, and an image produced by light of two or more different predetermined ranges of wavelengths. For example, non-visible light may be used to capture an image that shows heat distribution in the user's body, which may provide an indication of blood flow within the user, which in turn may be used to infer a condition of the user (e.g., a force being exerted by a finger of the user may have a different blood-flow pattern than a finger that is not exerting force).

A camera may be mounted on the user (e.g., on an head-mounted display worn by the user, or on a glove worn on the user's hand) or may be mounted external to the user to capture the user and/or the user's environment. When a camera is mounted on the user, the camera may be used to capture the user's environment and/or portions of the user's body (e.g., a hand-mounted camera may be used to capture an image of the user's other hand).

Figure 10:
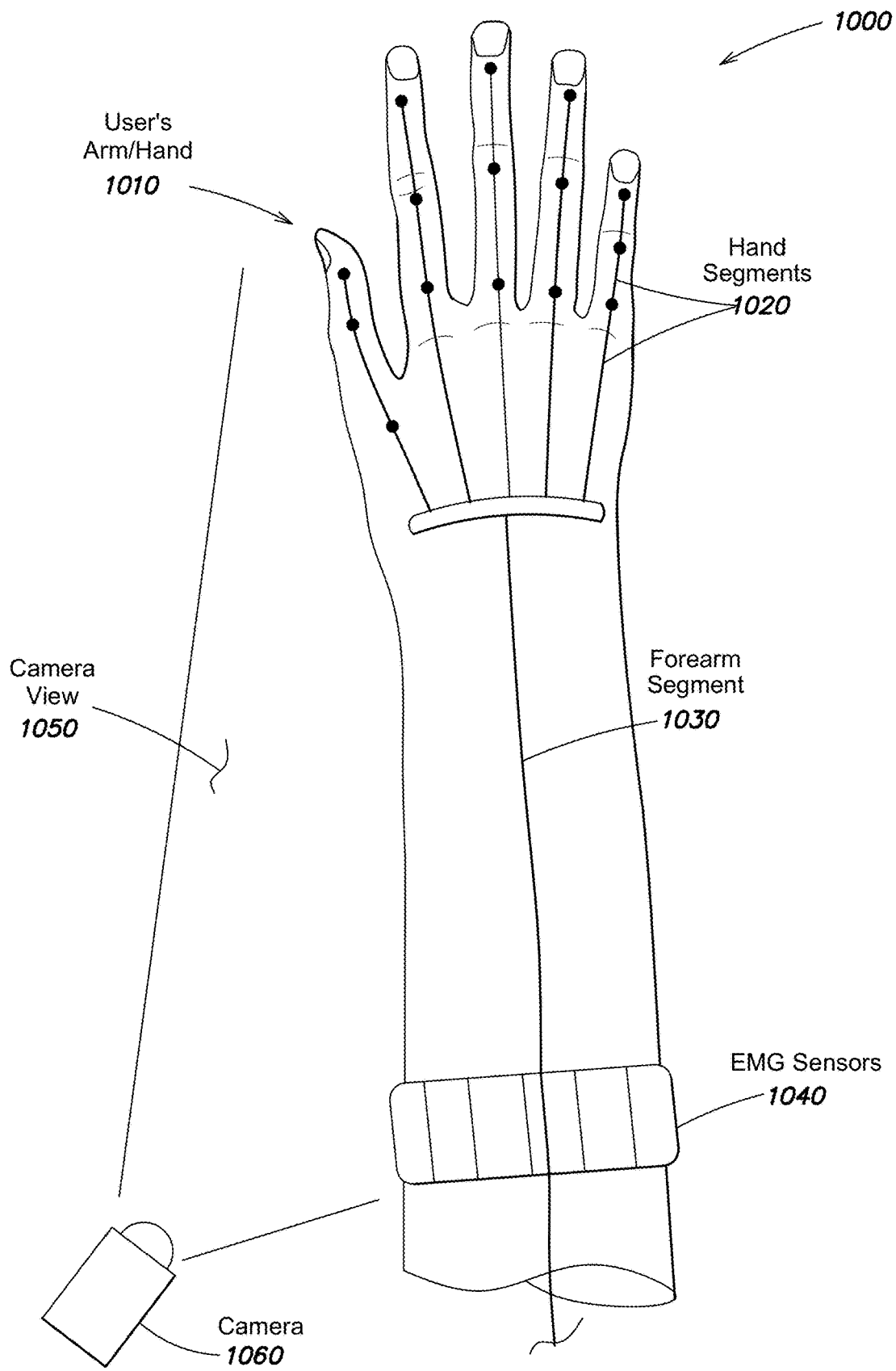
FIG. 10 is a diagram schematically showing an example of an implementation using EMG sensors and a camera, in accordance with some embodiments of the technology described herein.

FIG. 10 is a diagram showing an example implementation of a system 1000 that utilizes one or more EMG sensor(s) 1040 and a camera 1060, in accordance with some embodiments of the technology described herein. For example, FIG. 10 shows a user's arm and an attached hand ("arm/hand") 1010, which is made up of one or more joints and segments, and which can be depicted as a musculoskeletal representation. More particularly, the user's hand segments 1020 are connected by joints. The arm and hand positions and segment lengths of the arm and the hand can be determined by the system 1000 and positioned within a three-dimensional space of a model musculoskeletal representation. Further, the user's hand may also include an interpolated forearm segment 1030. As discussed above, a neuromuscular activity system may be used to determine one or more representations of a user's hand/arm positions. To this end, the user may wear a band comprising the one or more EMG sensor(s) 1040, which sense and record neuromuscular signals that are used to determine a musculoskeletal skeletal representation. Concurrently with the EMG sensor(s) 1040 sensing and recording the neuromuscular signals, a camera 1060 may be used to capture objects within the camera's field of view 1050. For example, in FIG. 10, the camera's field of view 1050 include the user's arm/hand 1010. Camera data in addition to the neuromuscular activity signals determined by the EMG sensors 1040 may be used to reconstruct positions, geometries, and forces being applied by the user's arm/hand 1010. Further, outputs from the system 1000 can be provided that allow the system 1000 to render a representation of the user's arm/hand 1010, such as within an AR environment of an AR system.

Figure 2:
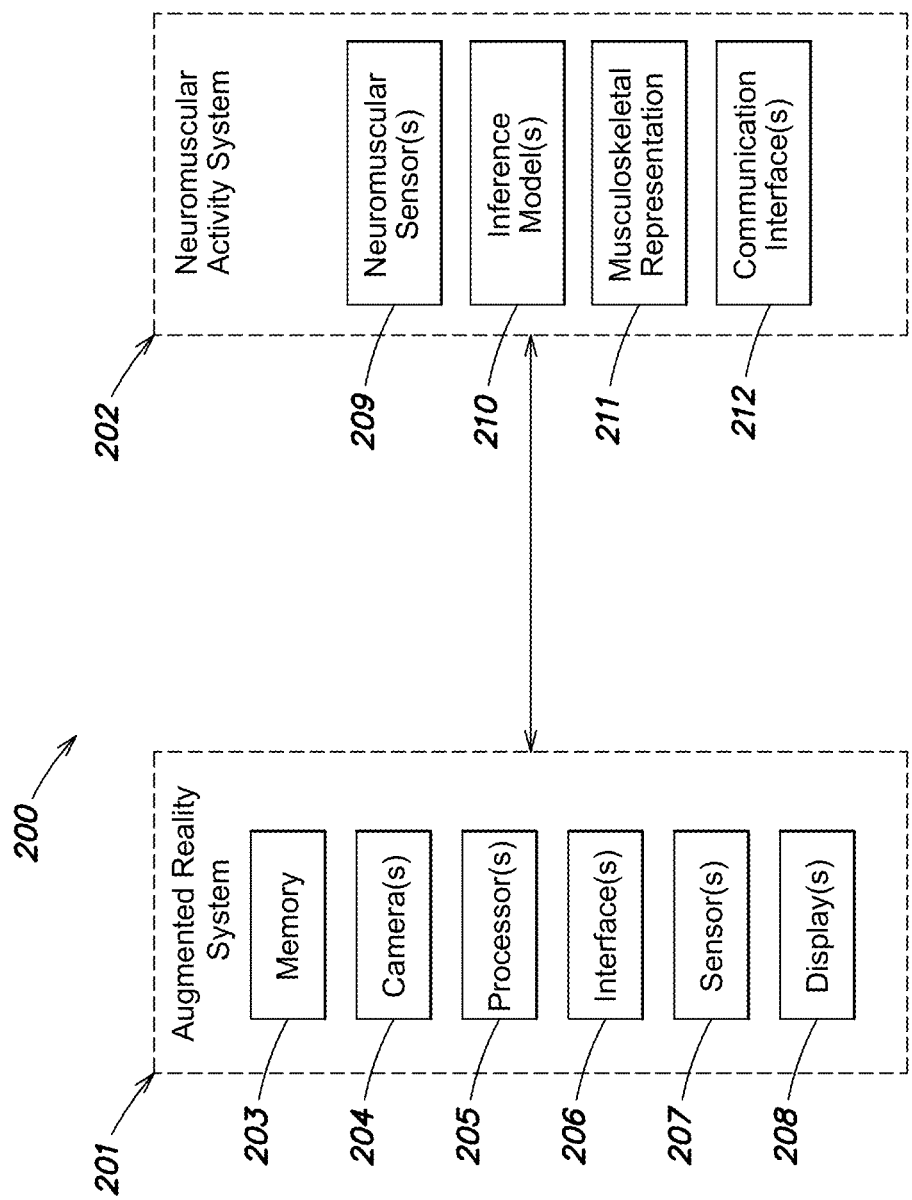
FIG. 2 is a schematic diagram of a distributed computer-based system that integrates an AR system with a neuromuscular activity system, in accordance with some embodiments of the technology described herein.

FIG. 2 illustrates a schematic diagram of an AR-based system 200, which may be a distributed computer-based system that integrates an AR system 201 with a neuromuscular activity system 202. The neuromuscular activity system 202 is similar to the system 100 described above with respect to FIG. 1.

Generally, an XR system such as the AR system 201 may take the form of a pair of goggles or glasses or eyewear, or other type of display device that shows display elements to a user that may be superimposed on the user's "reality." This reality in some cases could be the user's view of the environment (e.g., as viewed through the user's eyes), or a captured version (e.g., by camera(s)) of the user's view of the environment. In some embodiments, the AR system 201 may include one or more camera(s) 204, which may be mounted within a device worn by the user, that captures one or more views experienced by the user in the user's environment. The system 201 may have one or more processor(s) 205 operating within the device worn by the user and/or within a peripheral device or computer system, and such processor(s) 205 may be capable of transmitting and receiving video information and other types of data (e.g., sensor data).

The AR system 201 may also include one or more sensor(s) 207, such as microphones, GPS elements, accelerometers, infrared detectors, haptic feedback elements or any other type of sensor, or any combination thereof. In some embodiments, the AR system 201 may be an audio-based or auditory AR system, and the one or more sensor(s) 207 may also include one or more headphones or speakers. Further, the AR system 201 may also have one or more display(s) 208 that permit the AR system 201 to overlay and/or display information to the user in addition to provide the user with a view of the user's environment presented via the AR system 201. The AR system 201 may also include one or more communication interface(s) 206, which enable information to be communicated to one or more computer systems (e.g., a gaming system or other system capable of rendering or receiving AR data). AR systems can take many forms and are available from a number of different manufacturers. For example, various embodiments may be implemented in association with one or more types of AR systems or platforms, such as HoloLens holographic reality glasses available from the Microsoft Corporation (Redmond, Wash., USA); Lightwear AR headset from Magic Leap (Plantation, Fla., USA); Google Glass AR glasses available from Alphabet (Mountain View, Calif., USA); R-7 Smartglasses System available from Osterhout Design Group (also known as ODG; San Francisco, Calif., USA); Oculus Quest, Oculus Rift S, and Spark AR Studio available from Facebook (Menlo Park, Calif., USA); or any other type of AR or other XR device. Although discussed using AR by way of example, it should be appreciated that one or more embodiments of the technology disclosed herein may be implemented within one or more XR system(s).

The AR system 201 may be operatively coupled to the neuromuscular activity system 202 through one or more communication schemes or methodologies, including but not limited to, Bluetooth protocol, Wi-Fi, Ethernet-like protocols, or any number of connection types, wireless and/or wired. It should be appreciated that, for example, the systems 201 and 202 may be directly connected or coupled through one or more intermediate computer systems or network elements. The double-headed arrow in FIG. 2 represents the communicative coupling between the systems 201 and 202.

As mentioned above, the neuromuscular activity system 202 may be similar in structure and function to the system 100 described above with reference to FIG. 1. In particular, the system 202 may include one or more neuromuscular sensor(s) 209, one or more inference model(s) 210, and may create, maintain, and store a musculoskeletal representation 211. In an example embodiment, similar to one discussed above, the system 202 may include or may be implemented as a wearable device, such as a band that can be worn by a user, in order to collect (i.e., obtain) and analyze neuromuscular signals from the user. Further, the system 202 may include one or more communication interface(s) 212 that permit the system 202 to communicate with the AR system 201, such as by Bluetooth, Wi-Fi, or other communication method. Notably, the AR system 201 and the neuromuscular activity system 202 may communicate information that can be used to enhance user experience and/or allow the AR system 201 to function more accurately and effectively.

Although FIG. 2 shows a distributed computer-based system 200 that integrates the AR system 201 with the neuromuscular activity system 202, it will be understood that integration of these systems 201 and 202 may be non-distributed in nature. In some embodiments, the neuromuscular activity system 202 may be integrated into the AR system 201 such that the various components of the neuromuscular activity system 202 may be considered as part of the AR system 201. For example, inputs from the neuromuscular signals recorded by the neuromuscular sensor(s) 209 may be treated as another of the inputs (e.g., from the camera(s) 204, from the sensor(s) 207) to the AR system 201. In addition, processing of the inputs (e.g., sensor signals obtained) obtained from the neuromuscular sensor(s) 209 may be integrated into the AR system 201.

Figure 3:
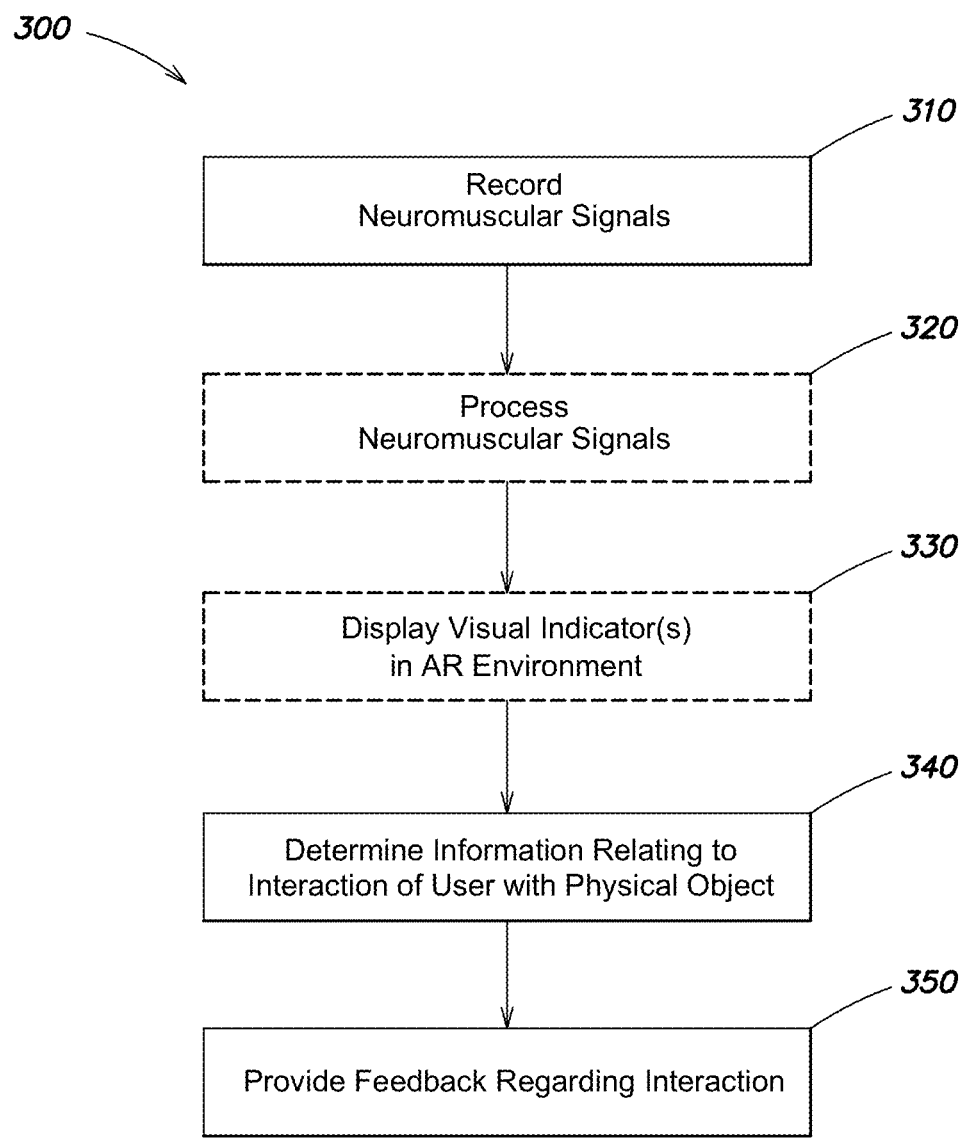
FIG. 3 is a flowchart of a process for using neuromuscular signals to provide an enhanced AR experience, in accordance with some embodiments of the technology described herein.

FIG. 3 illustrates a process 300 for using neuromuscular signals to provide a user with an enhanced interaction with a physical object in an AR environment generated by an AR system, such as the AR system 201, in accordance with some embodiments of the technology described herein. The process 300 may be performed at least in part by the neuromuscular activity system 202 and/or the AR system 201 of the AR-based system 200. At act 310, sensor signals (also referred to herein as "raw sensor signals") may be obtained (e.g., sensed and recorded) by one or more sensors of the neuromuscular activity system 202. In some embodiments, the sensor(s) may include a plurality of neuromuscular sensors 209 (e.g., EMG sensors) arranged on a wearable device worn by a user. For example, the sensors 209 may be EMG sensors arranged on an elastic band configured to be worn around a wrist or a forearm of the user to sense and record neuromuscular signals from the user as the user performs muscular activations (e.g., movements, gestures).

In some embodiments, the EMG sensors may be the sensors 704 arranged on the band 702, as shown in FIG. 7A; in some embodiments, the EMG sensors may be the sensors 810 arranged on the band 820, as shown in FIG. 8A. The muscular activations performed by the user may include static gestures, such as placing the user's hand palm down on a table; dynamic gestures, such as waving a finger back and forth; and covert gestures that are imperceptible to another person, such as slightly tensing a joint by co-contracting opposing muscles, or using sub-muscular activations. The muscular activations performed by the user may include symbolic gestures (e.g., gestures mapped to other gestures, interactions, or commands, for example, based on a gesture vocabulary that specifies the mapping).

In addition to the plurality of neuromuscular sensors 209, in some embodiments of the technology described herein, the neuromuscular activity system 202 may include one or more auxiliary sensor(s) configured to obtain (e.g., sense and record) auxiliary signals that may also be provided as input to the one or more trained inference model(s), as discussed above. Examples of auxiliary sensors include IMUs, imaging devices, radiation detection devices (e.g., laser scanning devices), heart rate monitors, or any other type of biosensors able to sense biophysical information from a user during performance of one or more muscular activations. Further, it should be appreciated that some embodiments of the present technology may be implemented using camera-based systems that perform skeletal tracking, such as, for example, the Kinect system available from the Microsoft Corporation (Redmond, Wash., USA) and the LeapMotion system available from Leap Motion, Inc. (San Francisco, Calif., USA). It should be appreciated that any combination of hardware and/or software may be used to implement various embodiments described herein.

The process 300 then proceeds to act 320, where raw sensor signals, which may include signals sensed and recorded by the one or more sensor(s) (e.g., EMG sensors, auxiliary sensors, etc.), as well as optional camera input signals from one more camera(s), may be optionally processed. In some embodiments, the raw sensor signals may be processed using hardware signal-processing circuitry (e.g., to perform amplification, filtering, and/or rectification). In other embodiments, at least some signal processing of the raw sensor signals may be performed using software. Accordingly, signal processing of the raw sensor signals, sensed and recorded by the one or more sensor(s) and optionally obtained from the one or more camera(s), may be performed using hardware, or software, or any suitable combination of hardware and software. In some implementations, the raw sensor signals may be processed to derive other signal data. For example, accelerometer data obtained by one or more IMU(s) may be integrated and/or filtered to determine derived signal data associated with one or more muscle(s) during activation of a muscle or performance of a gesture.

The process 300 then proceeds to act 330, where one or more visual indicators may be optionally displayed in the AR environment, based, at least in part, on the neuromuscular signals obtained by the plurality of neuromuscular sensors 209. For example, the AR system 201 may operate in conjunction with the neuromuscular activity system 202 to overlay one or more visual indicators on or near a physical object within the AR environment. The one or more visual indicators may instruct the user that the physical object is an object that has a set of virtual controls associated with it such that, if the user interacted with the object (e.g., by picking it up), the user could perform one or more "enhanced" or "augmented" interactions with the object. The one or more visual indicator(s) may be displayed within the AR environment in any suitable way. For example, the physical object may change colors or glow, thereby indicating that it is an object capable of enhanced interaction. In another example, an indication of a set of virtual controls for the physical object, which may be activated by the user to control the physical object, may be overlaid on or displayed near the physical object in the AR environment. The user may interact with the indicator(s) of the set of virtual controls by, for example, performing a muscular activation to select one of the virtual controls. In response to the interaction of the user with the indicator(s) of the set of virtual controls, information relating to an interaction with the physical object may be determined. For example, if the physical object is a writing implement and a displayed indicator of the set of virtual controls indicates that the user may use the writing implement as a pen, a paintbrush, or a pointing device within the AR environment, the user may perform a gesture to select a paintbrush functionality, such that, when the user picks up the writing implement, it may be used to paint within the AR environment.

The process 300 then proceeds to act 340, where information relating to an interaction of the user with the physical object is determined, based, at least in part, on the neuromuscular signals obtained by the plurality of neuromuscular sensors 209 and/or information derived from the neuromuscular signals. Optionally, auxiliary signals from one or more auxiliary device(s) (e.g., a camera, an IMU, etc.) may supplement the neuromuscular signals to determine the information relating to the interaction of the user with the physical object. For example, based, at least in part, on the neuromuscular signals (and optionally supplemented with auxiliary signals), the AR-based system 200 may determine how tightly the user is grasping the physical object, and a control signal may be sent to the AR-based system 200 based on an amount of grasping force being applied to the physical object. Continuing with the example above, the physical object may be a writing implement, and applying different amounts of grasping force to a surface of the writing implement and/or pressing on different parts of the writing implement may transform the writing implement into an "enhanced" or "augmented" writing implement in which a set of virtual control actions for the physical object may be enabled or activated.

In some embodiments, the information relating to the interaction of the user with the physical object in the AR environment may be determined based on a combination of the neuromuscular signals and at least one other sensor (e.g., a camera, an IMU, etc.). For example, some embodiments may include at least one camera (e.g., as part of the AR system 201), which may be arranged or configured to capture one or more images. An example of such an arrangement is shown in FIG. 10. The neuromuscular signals obtained by the plurality of neuromuscular sensors 209 and the image(s) captured by the camera(s) may be used, for example, to determine a force that that the user is applying to the physical object. Neuromuscular signal data and auxiliary sensor data (e.g., camera data) may be combined in any other suitable way to determine information associated with the user's interaction with the physical object, and embodiments are not limited in this respect.

The process 300 then proceeds to act 350, where feedback based on the determined information about the interaction of the user with the physical object is provided. In some embodiments, the feedback is provided to the user interacting with the object. For example, the AR-based system 200 may provide feedback (e.g., visual feedback, auditory feedback, haptic feedback) to the user within the AR environment. In embodiments where visual feedback is provided within the AR environment, the visual feedback may be provided in any suitable way. For example, the physical object with which the user is interacting may change colors or glow indicating that the user is interacting with the object. Alternatively, the feedback may be provided using a visual indicator separate from the physical object. For example, an icon or other visual indicator may be displayed within the AR environment showing an interaction mode (e.g., paintbrush mode) for the object with which the user is interacting. In some embodiments that provide feedback to the user, the feedback may be provided using non-visual forms of feedback such as auditory or haptic feedback. The feedback may, for example, instruct the user that the physical object that he/she is interacting with may have augmented properties or functions that may not be available through ordinary real-world interactions with the object.

In some embodiments of the technology described herein, the AR system (e.g., the system 201) may include haptic circuitry able to deliver haptic signals to the user. The haptic signals may be used to provide feedback to the user, and may comprise any one or any combination of a vibration actuator, a skin-tap actuator, a low-voltage electrical jolt circuit, and a force actuator. Such haptic actuators are known in the art, and my involve electromagnetic transducers, motors, and the like. The haptic circuitry may be arranged on a wearable device worn by the user, and may be included on a wearable patch or a wearable band, such as those discussed above. For example, the haptic circuitry may be included on the band 702 together with one or more neuromuscular sensor(s).

The AR system may be controlled to provide feedback to the user as haptic feedback delivered via the haptic circuitry. In some embodiments, the AR system may be controlled in this regard by a controller within the AR system or by a controller of the AR-based system (e.g., the system 200) encompassing the AR system. In other embodiments, the AR system may be controlled in this regard by control signals from a controller external to the AR system and external to the AR-based system.

In some embodiments, feedback may be provided to the user as an altered functionality of the physical object itself, rather than being provided as an indication separate from the altered functionality. For example, feedback may be provided to the user based on a current functionality of one or more physical object(s). Using the example above, the user may pick up a writing implement in the AR environment and grip the writing implement with a certain amount of force. Gripping the writing implement with a particular amount of force may transform the physical writing implement into an augmented writing implement (or AR writing implement), which may have different writing characteristics for writing within the AR environment. When the user uses the augmented writing implement to write within the AR environment, an augmented functionality of the writing implement may be apparent through use of the physical object itself to write. For example, a color of writing produced by the augmented writing implement, and/or a pixel size of writing produced by the augmented writing implement, and/or some other writing characteristic or combination of writing characteristics may provide feedback about the augmented functionality of the physical object.

In some embodiments, feedback may be provided to someone other than the user interacting with the physical object. For example, in a shared AR environment that includes a first user who is interacting with the object and a second user who is not interacting with the object, an indication may be provided to the second user about an interaction between the first user and the physical object in the AR environment. Such feedback may enable the second user to understand how the first user is interacting with the physical object as well as one or more other physical object(s) in the AR environment without directly observing the first user interacting with the object. For example, the second user may be able to determine how forceful the first user is grasping a ball in the AR environment, which may not be visibly apparent by observing an interaction of the first user with the ball.

The feedback provided at act 350 may reflect information relating to the interaction of the user with the physical object in any suitable way. For example, in some embodiments, the information relating to the interaction may include force information relating to a force that the user is applying to the object (e.g., by pressing, grasping, etc.). In such embodiments, a visual rendering of the force may be displayed within the AR environment to let the user (or another user in a shared AR environment) visualize an amount of force being applied to the object. In other embodiments in which force information is included in the information relating to the interaction, the feedback may be provided using a non-visual technique. For example, auditory and/or haptic feedback may be provided, based, at least in part, on an amount of force being applied to the object.

As discussed above, in some embodiments of the technology disclosed herein, physical objects in an AR environment may be transformed into "augmented" objects. An augmented object may have a set of enhanced or augmented features in the AR environment, and such augmented features may not be available when the user interacts with the object in a real-world environment. For example, a writing implement, such as a pen, may typically be capable of writing only in a single color of ink supplied in the pen, and using a line width dictated in part by a tip of the pen. In some embodiments, such a pen may be transformed into an augmented pen endowed with a set of augmented features for use within the AR environment. For example, an augmented writing implement when used within the AR environment may have a set of augmented features that enable a selection from among multiple writing colors, line thicknesses, brush shapes, tip shapes, drawing modes (e.g., a pen up/down functionality such that writing only occurs when a certain amount of pressure is applied to the writing implement), and writing-implement types (e.g., paintbrush, spray can, pen, pencil, highlighter). In some embodiments, the augmented features may also include functions not typically associated with use of the object in a real-world environment. For example, an augmented writing implement may be used as a remote controller or as a pointer within the AR environment, for selection and/or manipulation of one or more other object(s) at a distance from the user in the AR environment. In yet further embodiments, a physical object that is not typically used as a writing implement (e.g., a stick, ruler, or other object that can be held in the user's hand) may be transformed into a writing implement for use within the AR environment, based, at least in part, on the user's interaction with the physical object. For example, the user may pick up a physical object (e.g., a stick) in their environment and "double grasp" the object (i.e., grasp the object twice) with greater than a threshold amount of force to transform the object into a writing instrument within the AR environment, thereby transforming the physical object into an augmented object that may be used for providing writing input within the AR environment.

In some embodiments, selection by the user (e.g., selection of a physical object and/or a function relating to the physical object) may be performed based, at least in part, on user context and/or user behavior. For example, selection of a physical object may be based, at least in part, on user behavior such as information about one or more recent interactions between the user and one or more physical objects. In another example, if the user had most recently controlled a particular device such as a smart speaker by pressing play on a new track, then the smart speaker may be automatically selected, and a muscular activation determined based, at least in part, on the sensed neuromuscular signals may be used to change the volume of the selected smart speaker. In a further example, selection of a physical object may be based, at least in part, on user context such as information about a current location of the user (e.g., which environment (e.g., room) the user currently is located). The information about the user's current location may be determined in any suitable way including, but not limited to, using NFC technology, RFID technology, another field-based technology, and a global positioning technology (e.g., GPS). Based, at least in part, on the location information, a physical object in the user's environment (e.g., a light switch in a particular room) may be selected for control.

Figure 4:
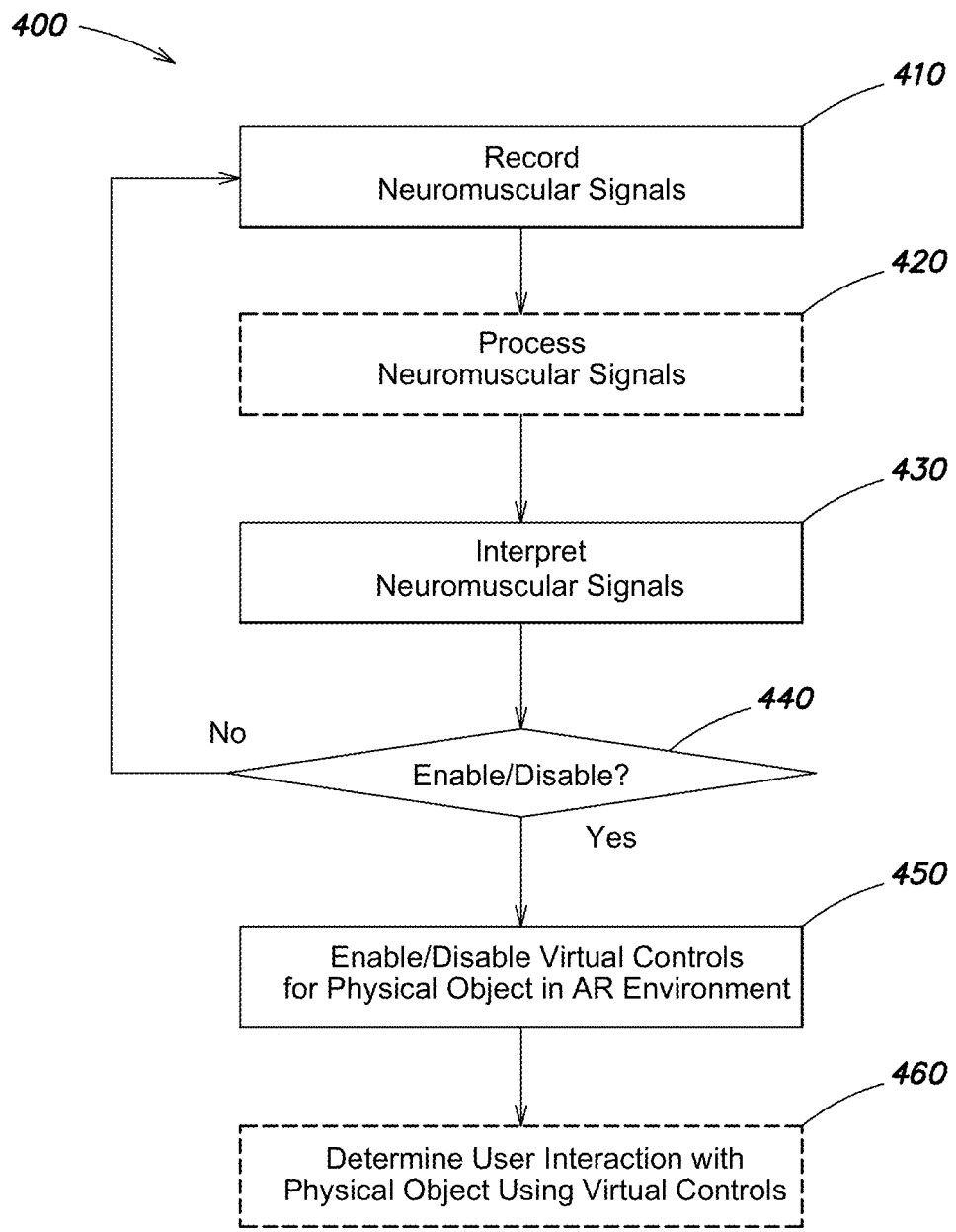
FIG. 4 is a flowchart of a process for providing virtual controls for physical objects in an AR environment, in accordance with some embodiments of the technology described herein.

FIG. 4 illustrates a process 400 for enabling and/or disabling virtual controls associated with an object in an AR environment, in accordance with some embodiments of the technology disclosed herein. At act 410, a plurality of neuromuscular signals are obtained by a plurality of neuromuscular sensors (e.g., the neuromuscular sensors 209) worn by a user. For example, the plurality of neuromuscular signals may be sensed and recorded by the plurality of neuromuscular sensors. The process 400 then proceeds to act 420, at which the plurality of neuromuscular signals may be optionally processed (e.g., amplified, filtered, rectified, etc.), examples of which are discussed above. The process 400 then proceeds to act 430, at which the plurality of neuromuscular signals and/or information derived from the plurality of neuromuscular signals are interpreted to, for example, determine a muscular activation performed by the user. Examples of interpreting neuromuscular signals may include, but are not limited to, processing the plurality of neuromuscular signals using one or more trained inference model(s) (e.g., the inference model(s) 114) to identify a muscular activation state that the user has performed, determining an amount of force applied to an object with which the user is interacting (e.g., an amount of force used to hold or grasp the object, an amount of force used to push against a stationary surface such as a table, etc.), determining co-contraction forces, and determining sub-muscular activation (e.g., activation of a single motor unit).

The process 400 then proceeds to act 440, where it is determined whether a set of virtual controls is to be enabled (if currently disabled) or disabled (if currently enabled), based, at least in part, on the interpreted neuromuscular signals. Determining whether to enable or disable a set of virtual controls may be made in any suitable way. Some embodiments map a particular muscle activation state (e.g., a particular gesture, or a particular muscle tension, or a particular sub-muscular activation, or any combination thereof) to a control signal for enabling or disabling the set of virtual controls associated with a physical object. For example, in some embodiments, the neuromuscular activity system (e.g., the neuromuscular activity system 202) may be configured to associate a pinch gesture involving the user's thumb and index finger with a command to enable or disable the set of virtual controls for the physical object. In other embodiments, the neuromuscular activity system may be configured to associate detection of a particular amount of force applied to the object with which the user is interacting with a command to enable or disable the set of virtual controls for the physical object. The amount of force applied to the object may be a static amount of force applied at a single point in time or a dynamic sequence of forces applied to the object (e.g., a double-squeeze of the object may enable or disable the set of virtual controls). In yet other embodiments, the neuromuscular activity system may be configured to associate activation of a single motor unit, or activation of a defined set of motor units, with a command to enable or disable the set of virtual controls for the physical object. At act 440, an output of the neuromuscular signal interpretation process at act 430 may be compared against stored information associating a muscle activation state or states to a control signal for enabling or disabling the set of virtual controls for the physical object to determine whether to enable or disable the set of virtual controls for the object. In some embodiments, the same muscle activation state(s) may be used to enable and disable virtual controls for all physical objects in the AR environment. In other embodiments, different muscle activation states may be associated with enabling and disabling virtual controls for different objects in the AR environment.

In some embodiments, the AR-based system (e.g., the system 200) may be configured to automatically enable virtual controls for physical objects in the AR environment without requiring the user to perform a muscular activation. For example, components of the AR-based system may be configured to determine which physical object(s) in the user's proximity that have virtual controls associated with the object(s), and the AR-based system may automatically enable virtual controls for those physical objects, and optionally may provide appropriate feedback to the user and/or one or more other user(s) (e.g., in a shared AR environment). Alternatively, the AR-based system may automatically enable virtual controls for a particular physical object in response to the user interacting with the object (e.g., when the user touches the object). Regardless of whether the AR-based system automatically enables virtual controls for object(s) or whether the user is required to perform muscular activation to enable the virtual controls, the AR-based system may disable virtual controls for an object in response to interpreting neuromuscular signals obtained from the user and/or information derived from the neuromuscular signals. In some embodiments, the muscular activation state(s) used to enable the virtual controls are the same as the muscular activation state(s) used to disable the virtual controls. In other embodiments, the muscular activation states used to enable and disable virtual controls for one or more object(s) in the AR environment are different.

If it is determined at act 440 that the virtual controls for the physical object in the AR environment should be enabled or disabled, the process proceeds to act 450, at which the virtual controls for the physical object are enabled or disabled. For example, a control signal may be sent to the AR system (e.g., the system 201) instructing the AR system to enable or disable virtual controls for a particular physical object, all physical objects within proximity of the user within the AR environment, or all physical objects within the user's field of view within the AR environment. In some embodiments, enabling a set of virtual controls for a physical object comprises providing an indication that the physical object has been transformed into an augmented object to which the virtual controls apply. Examples of providing an indication may include, but are not limited to, providing a visual, an audio, and/or a haptic indication within the AR environment to the user.

When virtual controls for an augmented or enhanced physical object are enabled, the process 400 optionally may proceed to act 460, where an interaction of the user with the object using the enabled set of virtual controls is determined. For example, if the augmented physical object is a writing implement and a set of enabled augmented features for the object includes a paintbrush mode, a pointer mode, and a remote control mode, the user may select one of the three modes by performing different muscular activations sensed and interpreted by the neuromuscular activity system (e.g., the system 202).

An AR environment may include a plurality of physical objects with which a user can interact. One or more of the plurality of physical objects in the AR environment may have a set of control actions associated with it. For example, as discussed above, the AR system (e.g., the system 201) of the AR-based system (e.g., the system 200) may be configured to associate a set of virtual controls with a physical object in the AR environment, and neuromuscular control signals obtained by the neuromuscular activity system (e.g., the system 202) may be used to enable or activate the set of virtual controls. From among the plurality of physical objects in the AR environment, the AR system may determine which object the user is interacting with, and may activate an appropriate set of control actions for the determined object.

Figure 5:
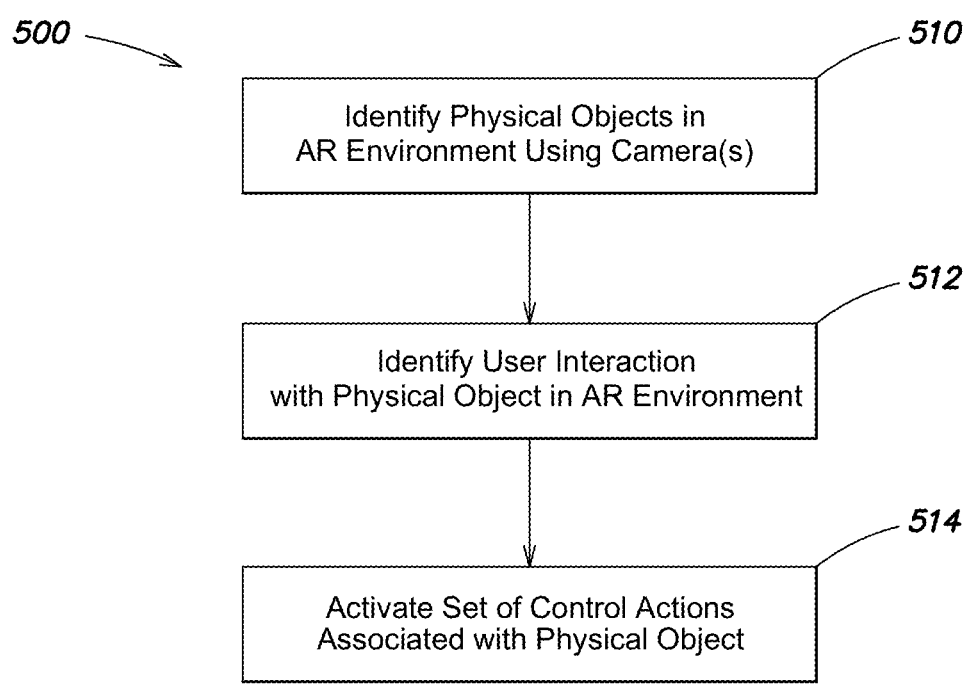
FIG. 5 is a flowchart of a process for activating a set of control actions for a physical object in an AR environment, in accordance with some embodiments of the technology described herein.

As described herein, AR components (e.g., cameras, sensors, etc.) may be used in combination with a neuromuscular controller (e.g., the one or more controller(s) 116) to provide enhanced functionally for interacting with physical objects in an AR environment. FIG. 5 illustrates a process 500 for activating a set of control actions associated with a physical object, in accordance with some embodiments of the technology disclosed herein. At act 510, physical objects in the AR environment are identified using one or more cameras (e.g., the camera(s) 204) associated with the AR-based system (e.g., the system 200). Images captured by camera(s) may be particularly useful in mapping environments and identifying physical objects in an AR environment. For example, if the user of the AR-based system is located in the user's kitchen, the camera(s) associated with the AR-based system may detect multiple physical objects in the user's AR environment, such as a refrigerator, a microwave oven, a stove, a pen, or an electronic device on a kitchen counter. As described above, in some embodiments, at least some of the physical objects in the AR environment may be associated with virtual controls that, when enabled, allow the user to interact with the objects in ways not possible when the user interacts with the objects in a real-world environment. In one exemplary embodiment of the technology disclosed herein, visual feedback may be provided to the user in the AR environment, to help guide or instruct the user in the real world. For example, a set of dials in the real world may be represented in the AR environment with overlaid visual interfaces and/or graphics, to inform the user about each dial, e.g., a type of the dial, a setting range of the dial, a purpose of the dial, or another characteristic of the dial as it relates to the real world and the user's interaction with the dial in the real world. In another example, visual instructions may be overlaid onto piano keys in an AR environment to instruct a user in the real world how to play a song on the piano. In another exemplary embodiment, if the stove in the kitchen was recently used and the surface of the stove is still hot, the AR system can present a warning label to the user in the AR environment, so that the user can avoid getting burned by the stove in real life. As another example, the AR system can present status information in the AR environment, to provide the user with information regarding the status of physical objects, e.g., device battery life, whether the device is switched on or off, etc.

The process 500 then proceeds to act 512, where an interaction of the user with a physical object in the AR environment is identified. The identification of the interaction may be made, at least in part, based on one or more images captured by the camera(s) associated with the AR system. For example, it may be determined from the one or more images that the user is holding a physical object (e.g., a writing implement), touching an object (e.g., a surface of a table) or reaching toward an object (e.g., a thermostat on the wall). In some embodiments, the identification of the interaction of the user with the object and/or a determination of how the user is interacting with the object may be made based, at least in part, on a plurality of neuromuscular signals obtained (e.g., sensed and recorded) by wearable sensors, as described above. For example, it may be determined based, at least in part, on the neuromuscular signals that the user is interacting with an object by pushing against the object with a force. After identifying the user's interaction with a physical object, the process 500 proceeds to act 514, where a set of control actions associated with the object with which the user is interacting is activated. For example, the set of control actions may be virtual controls, examples of which are described above.

In some embodiments, an interpretation of the neuromuscular signals by at least one trained inference model may be based, at least in part, on a particular object that the user is interacting with. For example, information about the physical object and/or information associated with an activated set of control actions may be provided as input to the trained inference model used to interpret the neuromuscular signals.

In some embodiments, an operation of the AR-based system may be modified based, at least in part, on an interaction of the user with a physical object in the AR environment. For example, a mode of the AR-based system may be changed from a coarse interaction mode (e.g., to determine whether a user is interacting with a physical object in the AR environment) into a higher-precision interaction mode for detecting finer-grained (e.g., more subtle or more detailed) interactions of the user with the physical object. The finer-grained interactions may include information about how the user is interacting with the physical object to perform different tasks within the AR environment using the physical object. The higher-precision interaction mode of the AR-based system may, for example, weight the neuromuscular signals more strongly than input from other sensors (e.g., a camera of the AR-based system) when determining information about one or more interaction(s) of the user with one or more physical object(s) in the AR environment.

In some embodiments, the neuromuscular signals may be used, at least in part, to affect how objects within the AR environment are digitized or rendered by the AR system. For some embodiments, AR applications may use one or more camera(s) to scan a physical environment to create a 3D model of the environment and physical objects within the physical environment so that, for example, virtual objects may be appropriately placed within an AR environment, which may be generated based on the physical environment, in a way that enables the virtual objects to interact properly with the physical objects in the AR environment. For example, a virtual character created within the generated AR environment may be presented as jumping up and down on a physical table in the AR environment. To ensure that the virtual character is represented within the AR environment correctly, properties about the table and its position are characterized in the 3D model of the physical environment created by the AR system. A potential limitation of camera-based scanning techniques for creating a 3D model of a physical environment is that non-visible properties of objects in the environment, which may include, but are not limited to, weight, texture, compressibility, bulk modulus, center of mass, and elasticity, are inferred from a visible appearance of the objects. In some embodiments, when a user interacts with a physical object in the physical environment (e.g., by picking up, pressing on, or otherwise manipulating the object), information about at least one non-visible property of the object may be determined with more specificity based on the neuromuscular signals obtained by the wearable sensors worn by the user, and this information about the non-visible properties of the object may be used to create a more accurate model of the object in the AR environment. For instance, neuromuscular signals obtained while the user picks up a soft furry pillow may differ from neuromuscular signals obtained while the user picks up a can of cold soda. Differences in, e.g., texture, temperature, and/or elasticity of a physical object may not be readily visible but may be sensed by one or more neuromuscular sensor(s) and/or one or more auxiliary sensor(s) and provided as feedback to the user.

The above-described embodiments can be implemented in any of numerous ways. For example, the embodiments may be implemented using hardware, software, or a combination thereof. When implemented in software, code comprising the software can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware or with one or more processors programmed using microcode or software to perform the functions recited above.

In this respect, it should be appreciated that one implementation of the embodiments of the present invention comprises at least one non-transitory computer-readable storage medium (e.g., a computer memory, a portable memory, a compact disk, etc.) encoded with a computer program (i.e., a plurality of instructions), which, when executed on a processor (or multiple processors), performs the above-discussed functions of the embodiments of the technologies described herein. The at least one computer-readable storage medium can be transportable such that the program stored thereon can be loaded onto any computer resource to implement the aspects of the present invention discussed herein. In addition, it should be appreciated that reference to a computer program which, when executed, performs the above-discussed functions, is not limited to an application program running on a host computer. Rather, the term computer program is used herein in a generic sense to reference any type of computer code (e.g., software or microcode) that can be employed to program a processor to implement the above-discussed aspects of the present invention. As will be appreciated, a first portion of the program may be executed on a first computer processor and a second portion of the program may be executed on a second computer processor different from the first computer processor. The first and second computer processors may be located at the same location or at different locations; in each scenario the first and second computer processors maybe in communication with each other via e.g., a communication network.

In some embodiments of the present technology provided herein, a kit may be provided for controlling an AR system. The kit may include a wearable device comprising a plurality of neuromuscular sensors configured to sense a plurality of neuromuscular signals of a user, and a non-transitory computer-readable storage medium encoded with a plurality of instructions that, when executed by at least one computer processor, causes the at least computer processor to perform a method for enabling a user to interact with a physical object in an AR environment generated by the AR system. The method may comprise: receiving, as input, the plurality of neuromuscular signals sensed from the user by the plurality of neuromuscular sensors; determining, based at least in part on the plurality of neuromuscular signals, information relating to an interaction of the user with the physical object in the AR environment generated by the AR system; and instructing the AR system to provide feedback based, at least in part, on the information relating to an interaction of the user with the physical object. For example, the wearable device may comprise a wearable band structured to be worn around a part of the user, or a wearable patch structured to be worn on a part of the user, as described above.

Various aspects of the present invention may be used alone, in combination, or in a variety of arrangements not specifically discussed in the embodiments described above and therefore are not limited in their application to the details and arrangement of components set forth in the foregoing description and/or illustrated in the drawings. For example, aspects described in one embodiment may be combined in any manner with aspects described in other embodiments.

Also, embodiments of the invention may be implemented as one or more methods, of which at least one example has been provided. The acts performed as part of the method(s) may be ordered in any suitable way. Accordingly, embodiments may be constructed in which acts are performed in an order different than illustrated and/or described, which may include performing some acts simultaneously, even though shown and/or described as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term).

The phraseology and terminology used herein is for the purpose of description and should not be regarded as limiting. The use of "including," "comprising," "having," "containing", "involving", and variations thereof, is meant to encompass the items listed thereafter and additional items.

Further, although advantages of the technology described herein may be indicated, it should be appreciated that not every embodiment of the invention will include every described advantage. Some embodiments may not implement any features described as advantageous herein. Accordingly, the foregoing description and attached drawings are by way of example only.

Variations on the disclosed embodiment are possible. For example, various aspects of the present technology may be used alone, in combination, or in a variety of arrangements not specifically discussed in the embodiments described in the foregoing, and therefore they are not limited in application to the details and arrangements of components set forth in the foregoing description or illustrated in the drawings. Aspects described in one embodiment may be combined in any manner with aspects described in other embodiments.

Use of ordinal terms such as "first," "second," "third," etc., in the description and/or the claims to modify an element does not by itself connote any priority, precedence, or order of one element over another, or the temporal order in which acts of a method are performed, but are used merely as labels to distinguish one element or act having a certain name from another element or act having a same name (but for use of the ordinal term) to distinguish the elements or acts.

The indefinite articles "a" and "an," as used herein in the specification and in the claims, unless clearly indicated to the contrary, should be understood to mean "at least one."

Any use of the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

Any use of the phrase "equal" or "the same" in reference to two values (e.g., distances, widths, etc.) means that two values are the same within manufacturing tolerances. Thus, two values being equal, or the same, may mean that the two values are different from one another by ±5%.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

The terms "approximately" and "about" if used herein may be construed to mean within ±20% of a target value in some embodiments, within ±10% of a target value in some embodiments, within ±5% of a target value in some embodiments, and within ±2% of a target value in some embodiments. The terms "approximately" and "about" may equal the target value.

The term "substantially" if used herein may be construed to mean within 95% of a target value in some embodiments, within 98% of a target value in some embodiments, within 99% of a target value in some embodiments, and within 99.5% of a target value in some embodiments. In some embodiments, the term "substantially" may equal 100% of the target value.

Having described several embodiments of the invention in detail, various modifications and improvements will readily occur to those skilled in the art. Such modifications and improvements are intended to be within the spirit and scope of the invention. Accordingly, the foregoing description is by way of example only, and is not intended as limiting. The invention is limited only as defined by the following claims and the equivalents thereto.

What is claimed is:

1. A computerized system for interacting with a physical object in an extended reality (XR) environment generated by an XR system, the computerized system comprising:
   a plurality of neuromuscular sensors configured to sense a plurality of neuromuscular signals from a user, wherein the plurality of neuromuscular sensors are arranged on one or more wearable devices worn by the user to sense the plurality of neuromuscular signals; and
   at least one computer processor programmed to:
      determine, based at least in part on the plurality of neuromuscular signals sensed by the plurality of neuromuscular sensors, information relating to an interaction of the user with the physical object in the XR environment generated by the XR system;
      instruct the XR system to provide feedback based, at least in part, on the information relating to the interaction of the user with the physical object; and
      instruct the XR system to provide the feedback to the user, wherein:
      the feedback provided to the user comprises an indication of an amount of force applied to the physical object by the user, and
      the amount of force is determined based, at least in part, on the plurality of neuromuscular signals and image data associated with the force applied to the physical object, wherein the image data comprises images captured using visable and non-visable light.

2. The computerized system of claim 1, wherein the at least one computer processor is further programmed to instruct the XR system to display at least one visual indicator on the physical object in the XR environment.

3. The computerized system of claim 2, wherein the at least one computer processor determines the information relating to the interaction of the user with the physical object based, at least in part, on an interaction of the user with the at least one visual indicator displayed on the physical object.

4. The computerized system of claim 1, wherein the at least one computer processor instructs the XR system to provide the feedback as visual feedback to the user within the XR environment.

5. The computerized system of claim 4, wherein the at least one computer processor instructs the XR system to provide the visual feedback to the user within the XR environment as a change in at least one property of at least one visual indicator displayed by the XR system.

6. The computerized system of claim 4, wherein the at least one computer processor instructs the XR system to provide the visual feedback to the user within the XR environment as a display of at least one new visual indicator associated with the physical object within the XR environment.

7. The computerized system of claim 4, wherein the at least one computer processor instructs the XR system to provide the feedback to the user as at least one of audio feedback or electrical stimulation feedback.

8. The computerized system of claim 1, wherein the at least one computer processor instructs the XR system to provide the feedback as a change in at least one function of the physical object when the at least one function is used within the XR environment.

9. The computerized system of claim 1, wherein:
the information relating to the interaction of the user with the physical object comprises information that the user has interacted with a particular physical object, and
the at least one computer processor instructs the XR system to provide the feedback as a modification of at least one interaction property of the particular physical object, and as an indication of the modification to the user.

10. The computerized system of claim 9, wherein the modification of the at least one interaction property of the particular physical object comprises an enablement of at least one virtual control associated with the particular physical object.

11. The computerized system of claim 10, wherein the at least one computer processor is programmed to disable the at least one virtual control associated with the particular physical object in response to receiving input from the user.

12. The computerized system of claim 11, wherein the at least one virtual control associated with the particular physical object is disabled by the at least one computer processor based, at least in part, on the plurality of neuromuscular signals.

13. The computerized system of claim 9, wherein:
the particular physical object comprises a writing implement, and
the modification of the at least one interaction property comprises activation of a set of augmented features for the writing implement.

14. The computerized system of claim 13, wherein the set of augmented features includes features that enable the user to interact with the writing implement in one or more ways to change one or more writing characteristics of the writing implement in the XR environment.

15. The computerized system of claim 1, wherein:
functions of the physical object in the XR environment are controlled by a set of virtual controls, and
the at least one computer processor is programmed to instruct the XR system, based at least in part on the plurality of neuromuscular signals, to perform any one or any combination of:
an activation of the set of virtual controls,
a deactivation of the set of virtual controls, and
a modification of the set of virtual controls.

16. The computerized system of claim 15, wherein the plurality of neuromuscular signals comprises signals arising from a gesture performed by the user, the gesture comprising any one or any combination of:
a static gesture,
a dynamic gesture,
a covert gesture,
a muscular activation state, and
a sub-muscular activation state.

17. The computerized system of claim 1, wherein:
the XR environment includes a plurality of physical objects,
each of the plurality of physical objects is associated with a set of control actions, and
the at least one computer processor is programmed to:
identify the physical object with which the user is interacting within the XR environment, and
activate a corresponding set of control actions associated with the identified physical object.

18. The computerized system of claim 17, wherein the feedback comprises a visual display within the XR environment, the visual display indicating the activated set of control actions.

19. The computerized system of claim 17 wherein the at least one computer processor is programmed to determine the information relating to the interaction of the user with the physical object based, at least in part, on the activated set of control actions.

20. The computerized system of claim 17, wherein the at least one computer processor:
determines the information relating to the interaction of the user with the physical object based, at least in part, on an output of an inference model to which the plurality of neuromuscular signals, or information derived from the plurality of neuromuscular signals, or the plurality of neuromuscular signals and the information derived from the plurality of neuromuscular signals are provided as input, and
prior to the output of the inference model being rendered, provides to the inference model information about the identified physical object, or information associated with the activated set of control actions, or the information about the identified physical object and the information associated with the activated set of control actions.

21. The computerized system of claim 1, wherein:
the XR environment includes a plurality of physical objects,
each of the plurality of physical objects is associated with a set of control actions, and
the at least one computer processor is programmed to instruct the XR system to:
select a particular physical object of the plurality of physical objects for active control in the XR environment, based at least in part on the plurality of neuromuscular signals; and
activate a corresponding set of control actions associated with the particular physical object.

22. The computerized system of claim 21, wherein the plurality of neuromuscular signals comprises signals arising from a gesture performed by the user, the gesture comprising any one or any combination of:
a static gesture,
a dynamic gesture,
a covert gesture,
a muscular activation state, and
a sub-muscular activation state.

23. The computerized system of claim 1, wherein the at least one computer processor is programmed to modify an operation of the XR system based, at least in part, on the information relating to the interaction of the user with the physical object.

24. The computerized system of claim 23, wherein the at least one computer processor modifies the operation of the XR system by instructing the XR system to enter a higher-precision mode for detecting finer-grained interactions of the user with the physical object.

25. The computerized system of claim 24, wherein, when in the higher-precision mode, the XR system uses a greater weight for the plurality of neuromuscular signals than a weight used for auxiliary signals from at least one auxiliary sensor, to determine the information relating to the interaction of the user with the physical object.

26. A method performed by a computerized system for enabling a user to interact with a physical object in an extended reality (XR) environment generated by an XR system based, at least in part, on neuromuscular signals, the method comprising:
obtaining a plurality of neuromuscular signals from a user using a plurality of neuromuscular sensors arranged on one or more wearable devices worn by the user to sense the plurality of neuromuscular signals;
determining, using at least one computer processor coupled to a memory storing code executed by the at least one computer processor, based at least in part on the plurality of neuromuscular signals, information relating to an interaction of the user with the physical object in the XR environment generated by the XR system;
instructing, using the at least one computer processor, the XR system to provide feedback based, at least in part, on the information relating to the interaction of the user with the physical object;
instructing, using the at least one computer processor, the XR system to enter a higher-precision mode for detecting finer-grained interactions of the user with the physical object; and
instructing, using the at least one computer processor, the XR system to provide the feedback as a change in at least one function of the physical object when the at least one function is used within the XR environment.

27. A non-transitory computer-readable medium encoded with a plurality of instructions that, when executed by at least one computer processor, causes the at least computer processor to perform a method for enabling a user to interact with a physical object in an extended reality (XR) environment generated by an XR system based, at least in part, on neuromuscular signals, the method comprising:
receiving, as input, a plurality of neuromuscular signals obtained from a user via a plurality of neuromuscular sensors arranged on one or more wearable devices worn by the user to sense the plurality of neuromuscular signals;
determining, based at least in part on the plurality of neuromuscular signals, information relating to an interaction of the user with the physical object in the XR environment generated by the XR system;
instructing the XR system to provide feedback based, at least in part, on the information relating to the interaction of the user with the physical object;
instructing the XR system to enter a higher-precision mode for detecting finer-grained interactions of the user with the physical object; and
instructing the XR system to provide the feedback as a modification of at least one interaction property of a particular physical object and as an indication of the modification to the user, wherein:
the information relating to the interaction of the user with the physical object comprises information that the user has interacted with the particular physical object,
the particular physical object comprises a writing implement, and
the modification of the at least one interaction property comprises activation of a set of augmented features for the writing implement.

28. An extended reality (XR) system comprising:
a wearable device comprising a plurality of neuromuscular sensors configured to sense a plurality of neuromuscular signals of a user; and
a non-transitory computer-readable medium encoded with a plurality of instructions that, when executed by at least one computer processor, causes the at least one computer processor to perform a method for enabling a user to interact with a physical object in an XR environment generated by the XR system, the method comprising:
receiving, as input, the plurality of neuromuscular signals sensed from the user by the plurality of neuromuscular sensors;
determining, based at least in part on the plurality of neuromuscular signals, information relating to an interaction of the user with the physical object in the XR environment generated by the XR system;
instructing the XR system to provide feedback based, at least in part, on the information relating to the interaction of the user with the physical object;
instructing the XR system to enter a higher-precision mode for detecting finer-grained interactions of the user with the physical object, wherein functions of the physical object in the XR environment are controlled by a set of virtual controls; and
performing, based at least in part on the plurality of neuromuscular signals, any one or any combination of:
an activation of the set of virtual controls,
a deactivation of the set of virtual controls, and
a modification of the set of virtual controls.

29. A computerized system for interacting with a physical object in an extended reality (XR) environment generated by an XR system, the computerized system comprising:
a plurality of neuromuscular sensors configured to sense a plurality of neuromuscular signals from a user, wherein the plurality of neuromuscular sensors are arranged on one or more wearable devices worn by the user to sense the plurality of neuromuscular signals; and
at least one computer processor programmed to:
determine, based at least in part on the plurality of neuromuscular signals sensed by the plurality of neuromuscular sensors, information relating to an interaction of the user with the physical object in the XR environment generated by the XR system;
instruct the XR system to provide feedback based, at least in part, on the information relating to the interaction of the user with the physical object;
instruct the XR system to enter a higher-precision mode for detecting finer-grained interactions of the user with the physical object, wherein the XR environment includes a plurality of physical objects, and each of the plurality of physical objects is associated with a set of control actions;
identify the physical object with which the user is interacting within the XR environment;
activate a corresponding set of control actions associated with the identified physical object;
determine the information relating to the interaction of the user with the physical object based, at least in part, on an output of an inference model to which at least one of the plurality of neuromuscular signals or information derived from the plurality of neuromuscular signals are provided as input; and
prior to the output of the inference model being rendered, provide to the inference model information about at least one of the identified physical object or information associated with the activated set of control actions.

30. A computerized system for interacting with a physical object in an extended reality (XR) environment generated by an XR system, the computerized system comprising:
a plurality of neuromuscular sensors configured to sense a plurality of neuromuscular signals from a user, wherein the plurality of neuromuscular sensors are arranged on one or more wearable devices worn by the user to sense the plurality of neuromuscular signals; and
at least one computer processor programmed to:
determine, based at least in part, on the plurality of neuromuscular signals sensed by the plurality of neuromuscular sensors, information relating to an interaction of the user with the physical object in the XR environment generated by the XR system;
instruct the XR system to provide feedback based, at least in part, on the information relating to the interaction of the user with the physical object;
instruct the XR system to enter a higher-precision mode for detecting finer-grained interactions of the user with the physical object; and
modify an operation of the XR system based, at least in part, on the information relating to the interaction of the user with the physical object.

* * * * *

UNITED STATES PATENT AND TRADEMARK OFFICE
CERTIFICATE OF CORRECTION

PATENT NO. : 10,970,936 B2  
APPLICATION NO. : 16/593446  
DATED : April 6, 2021  
INVENTOR(S) : Christopher Osborn et al.

Page 1 of 1

It is certified that error appears in the above-identified patent and that said Letters Patent is hereby corrected as shown below:

In the Claims

Claim 1, Column 42, Line 57 should read:
captured using visible and non-visible light.

Signed and Sealed this
Eleventh Day of May, 2021

Drew Hirshfeld
*Performing the Functions and Duties of the*
*Under Secretary of Commerce for Intellectual Property and*
*Director of the United States Patent and Trademark Office*